US010166253B2

(12) United States Patent
Jensen et al.

(10) Patent No.: US 10,166,253 B2
(45) Date of Patent: Jan. 1, 2019

(54) POSITIVELY CHARGED CO-POLYMERS FOR USE AS ANTIMICROBIAL AGENTS

(71) Applicants: Aarhus Universitet, Aarhus C (DK); Region Midtjylland, Viborg (DK)

(72) Inventors: Thomas Vorup Jensen, Aarhus N (DK); Stig Hill Christiansen, Aarhus C (DK); Jørgen Eskild Petersen, Vedbæk (DK)

(73) Assignees: Region Midtjylland, Vibord (DK); Aarhus Universitet, Aarhus C (DK)

( * ) Notice: Subject to any disclaimer, the term of this patent is extended or adjusted under 35 U.S.C. 154(b) by 0 days.

(21) Appl. No.: 15/506,375

(22) PCT Filed: Aug. 28, 2015

(86) PCT No.: PCT/DK2015/050254
§ 371 (c)(1),
(2) Date: Feb. 24, 2017

(87) PCT Pub. No.: WO2016/029920
PCT Pub. Date: Mar. 3, 2016

(65) Prior Publication Data
US 2017/0239288 A1    Aug. 24, 2017

(30) Foreign Application Priority Data
Aug. 29, 2014 (DK) .................................. 2014 70521

(51) Int. Cl.
| | |
|---|---|
| A61K 31/785 | (2006.01) |
| A61K 9/00 | (2006.01) |
| A61K 38/16 | (2006.01) |
| A61K 9/12 | (2006.01) |
| A61K 38/02 | (2006.01) |
| A61K 45/06 | (2006.01) |
| A61K 31/5377 | (2006.01) |
| A61K 31/7036 | (2006.01) |
| A61K 38/12 | (2006.01) |
| A61K 38/14 | (2006.01) |
| C08G 69/36 | (2006.01) |

(52) U.S. Cl.
CPC ............ *A61K 31/785* (2013.01); *A61K 9/007* (2013.01); *A61K 9/0073* (2013.01); *A61K 9/12* (2013.01); *A61K 31/5377* (2013.01); *A61K 31/7036* (2013.01); *A61K 38/02* (2013.01); *A61K 38/12* (2013.01); *A61K 38/14* (2013.01); *A61K 38/16* (2013.01); *A61K 45/06* (2013.01); *C08G 69/36* (2013.01); *Y02A 50/473* (2018.01)

(58) Field of Classification Search
None
See application file for complete search history.

(56) References Cited

U.S. PATENT DOCUMENTS

| | | | |
|---|---|---|---|
| 6,689,756 B2 * | 2/2004 | Hesson | A61K 31/43 514/192 |
| 7,033,582 B2 * | 4/2006 | Yong | A61K 31/785 424/400 |
| 2007/0032428 A1 | 2/2007 | Mor et al. | |
| 2009/0048181 A1 * | 2/2009 | Schipper | A61K 31/198 514/1.1 |

FOREIGN PATENT DOCUMENTS

| | | |
|---|---|---|
| WO | 0193828 A1 | 12/2001 |
| WO | 2006082581 A2 | 8/2006 |
| WO | 2010149795 A1 | 12/2010 |
| WO | 2012027411 A2 | 3/2012 |
| WO | 2013142374 A1 | 9/2013 |

OTHER PUBLICATIONS

Chang et al.; Infection (2000); 28:8-12. (Year: 2000).*
Christiansen, SH et al.; "The Immunomodulatory Drug Glatiramer Acetate is Also an Effective Antimicrobial Agent that Kills Gram-negative Bacteria.", Sci Rep. Nov. 15, 2017;7(1):15653.*
Abdelaziz, H. et al; "Inhibition of TNF-alfa production in THP-1 macrophages by glatiramer acetate does not alter their susceptibility to infection by Listeria monocytogenes and does not impair the efficacy of ampicillin or moxifloxacin against intracellular bacteria"; J Antimicrob Chemother. Jul. 2004;54(1):288-9.
Brogden, Kim A.; "Antimicrobial Peptides: Pore formers of Metabolic Inhibitors in Bacteria?", Nat Rev Microbiol. Mar. 2005;3(3):238-50.
Christiansen, Stig Hill et al; "The random co-polymer glatiramer acetate rapidly kills primary human leukocytes through sialic-acid-dependent cell membrane damage"; Biochimica et Biophysica Acta 1859; 2017; 425-437.
Deming, Timothy J. et al; "Synthetic polypeptides for biomedical applications"; Progress in Polymer Science, Pergamon Press, Oxford, GB; vol. 32, No. 8-9; Aug. 7, 2007; pp. 858-875.
Dorosz, Jerzy et al; Membrane Interactions of Novicidin, a Novel Antimicrobial Peptide: Phosphatidylglycerol Promotes Bilayer Insertion; J. Phys. Chem. B.; 2010; 114; 11053-11060.
Gilliam, H. et al; "Increased bronchial chloride concentration on cystic fibrosis"; Scand J Clin Lab Invest 1989: 49: 121-124.

(Continued)

*Primary Examiner* — Jeffrey T. Palenik
(74) *Attorney, Agent, or Firm* — Postemak Blankstein & Lund LLP

(57) ABSTRACT

The present invention provides a positively charged co-polymer for use as an antimicrobial agent, wherein said positively charged co-polymer is composed of amino acids and/or derivatives thereof and wherein at least 75 molar percent of said amino acids are selected from the group consisting of alanine, lysine, glutamate, arginine and tyrosine and/or derivatives thereof. The present invention also provides methods for treating, preventing or ameliorating a microbial infection comprising administration of positively charged random co-polymers as well as a pharmaceutical composition comprising said co-polymer. The invention further provides a kit of parts comprising the positively charged random co-polymer.

12 Claims, 13 Drawing Sheets

(56) References Cited

OTHER PUBLICATIONS

Giuliani, Fabrizio et al; "Additive effect of the combination of glatiramer acetate and minocycline in a model of MS"; Journal of Neuroimmunology, 158 (2005) 213-221.

Gorantla, S et al; "Modulation of Innate Immunity by Copolymer-1 Leads to Neuroprotection in Murine HIV-1-Encephalitis"; Glia. Jan. 15, 2008; 56(2): 223-232.

Habets, M. et al; "Therapeutic antimicrobial peptides may compromise natural immunity"; Biological Letters, Jan. 25, 2012; 8, 416-418.

Hartmann, M. et al; "Damage of the Bacterial Cell Envelope by Antimicrobial Peptides Gramicidin S and PGLa as Revealed by Transmission and Scanning Electron Microscopy"; Antimicrobial Agents and Chemotherapy; Aug. 2010, pp. 3132-3142; vol. 54, No. 8.

Henderson, J. M. et al; "Promising antimicrobial agents designed from natural peptide templates"; Current Opinion in Solid State and Materials Science; vol. 17, No. 4; Aug. 1, 2013, pp. 175-192.

Johansson, J. et al; Conformation-dependent Antibacterial Activity of the Naturally Occurring Human Peptide LL-37; The Journal of Biological Chemistry; vol. 273, No. 6, Issue 6 Feb. 2998; 3718-3724.

Lackner, P. et al, "Glatiramer acetate reduces the risk for experimental cerebral malaria: a pilot study"; Malaria Journal; 2009, 8:36.

Meincken, M et al; "Atomic Force Microscopy Study of the Effect of Antimicrobial Peptides on the Cell Envelope of *Escherichia coli*"; Antimicrobial Agents and Chemotherapy, vol. 49, No. 10; Oct. 2005; 4085-4092.

Noore, J. et al; "Cationic Antimicrobial Peptide LL-37 Is Effective against both Extra- and Intracellular *Staphylococcus aureus*"; Antimicrobial Agents and Chemotherapy, vol. 57, No. 3; Mar. 1, 2013; pp. 1283-1290.

Wang, Yuqin et al; "Apolipoprotein A-I Binds and Inhibits the Human Antibacterial/Cytotoxic Peptide LL-37"; The Journal of Biological Chemistry; vol. 273 No. 50; Dec. 11, 1998, 33115-33118.

Wiegand, Irith et al; "Agar and broth dilution methods to determine the minimal inhibitory concentration (MIC) of antimicrobial substances"; Nature Protocols; vol. 3, No. 2; 2008, pp. 163-175.

Zasloff, Michael; "Antimicrobial peptides of multicellular organisms"; Nature; Jan. 24;415(6870):389-95.

\* cited by examiner

Figure 1, continued
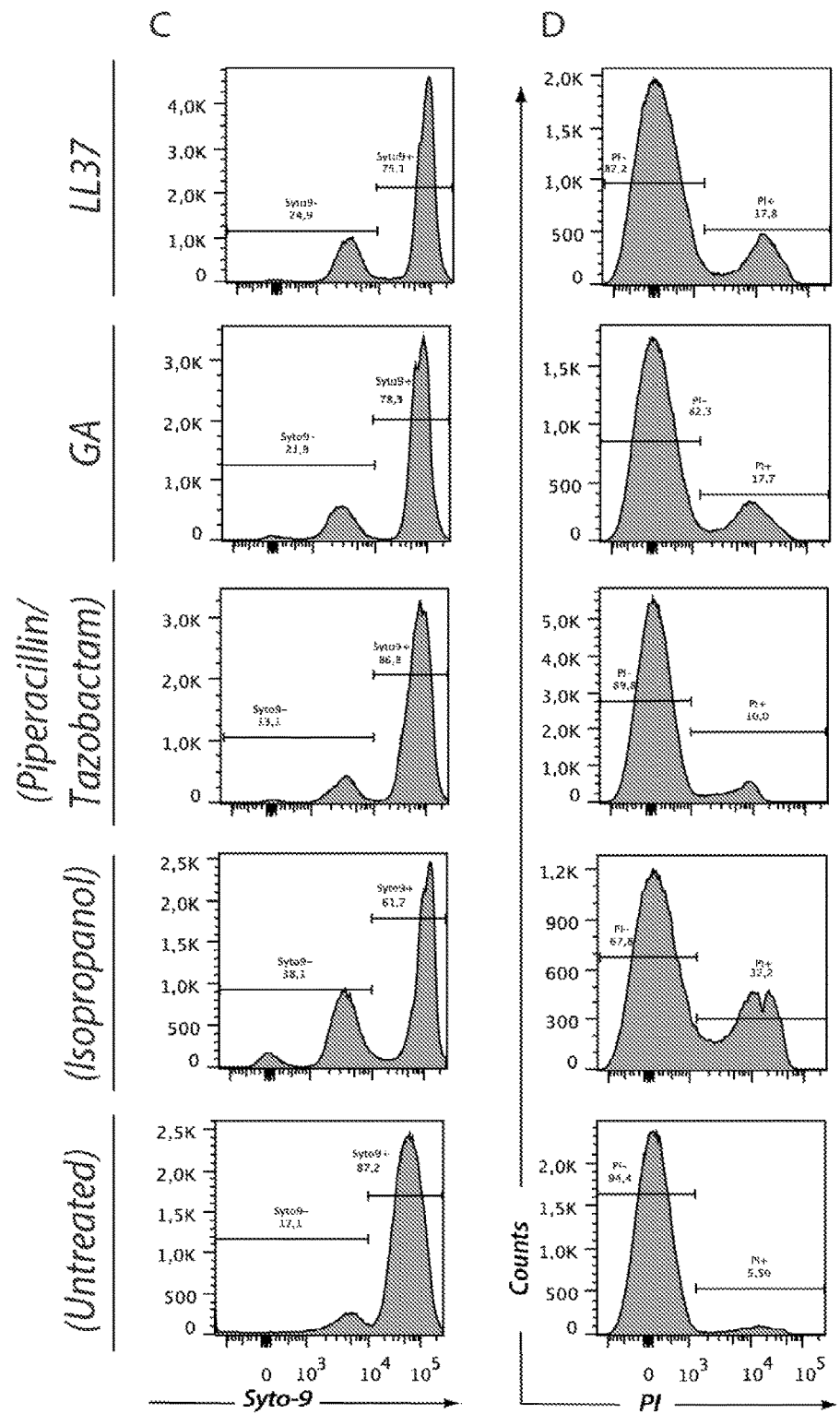

Figure 3, continued
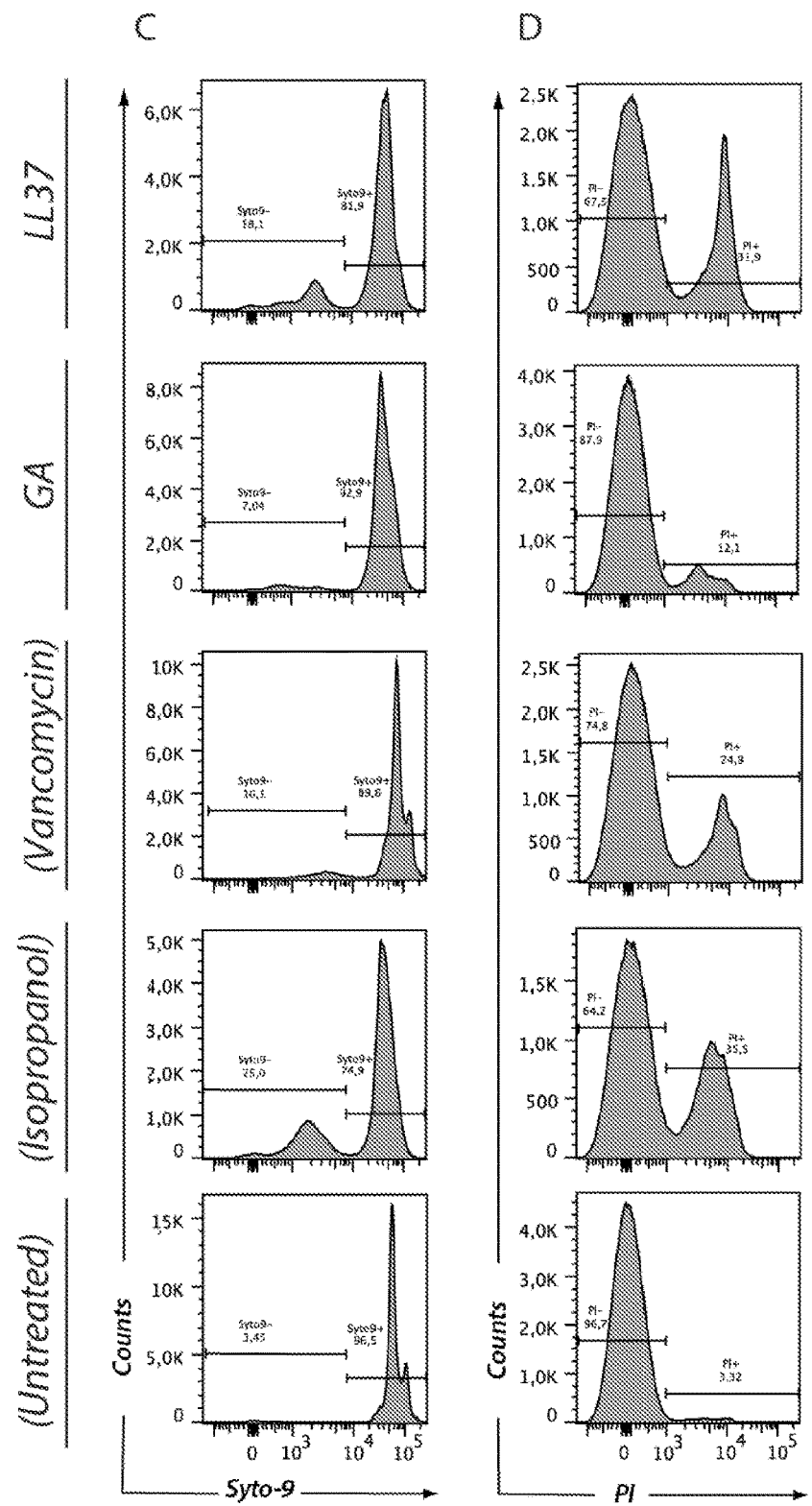

POSITIVELY CHARGED CO-POLYMERS FOR USE AS ANTIMICROBIAL AGENTS

FIELD OF INVENTION

The present invention provides a positively charged co-polymer for use as an antimicrobial agent, wherein said positively charged co-polymer is composed of amino acids and/or derivatives thereof and wherein at least 75 molar percent of said amino acids are selected from the group consisting of alanine, lysine, glutamate, arginine and tyrosine and/or derivatives thereof. The present invention also provides methods for treating, preventing or ameliorating a microbial infection comprising administration of positively charged random co-polymers as well as a pharmaceutical composition comprising said co-polymer. The invention further provides a kit of parts comprising the positively charged random co-polymer.

BACKGROUND OF INVENTION

In virtually any organism, immunity to infections is contributed by evolutionary conserved peptides with a striking ability to eradicate microbial organisms. Hence, named host defense peptides, or more frequently antimicrobial peptides (AMPs). AMPs are secreted as inactive precursors and proteolytically activated into potent antimicrobial peptides by serine proteases. The current dogma is that AMPs act to destabilize the cell membrane of microorganisms through electrostatic interactions between the cationic AMPs and the anionic microbial membrane (Zasloff, M., Antimicrobial peptides of multicellular organisms. Nature, 2002. 415(6870): p. 389-95). The electrostatic interactions allow these peptides to permeabilize the membrane lipid bilayer, thereby leading to the formation of membrane pores, cell depolarization, leakage of intracellular contents, and ultimately cell death (Brogden, K. A., *Antimicrobial peptides: pore formers or metabolic inhibitors in bacteria*? Nat Rev Microbiol, 2005. 3(3): p. 238-50). These proteins have consequently been considered as potential antibiotics for use in prevention or treatment of infections in humans. Unfortunately, the positive charge of these proteins also enables a range of unwanted effects on human cells. Most prominently, AMP such as ovispirin lyse human erythrocytes, whereas LL-37 has been shown to destroy human cells, including leukocytes, through destabilization of the cellular membrane (S. H. Christiansen, K. Juul-Madsen, B. Vad, M. Behrens, B. Jalilian, J. S. Pedersen, D. Otzen and and T. Vorup-Jensen et al., 2014, in preparation,).

While LL-37 and other similar peptides, in principal, could serve as agents useful for antimicrobial treatment in humans, conflicting observations suggest that the ability to destroy human cells hinders efficient clinical application (Dorosz, J., et al., *Membrane interactions of novicidin, a novel antimicrobial peptide: phosphatidylglycerol promotes bilayer insertion*. J Phys Chem B, 2010. 114(34): p. 11053-60). Furthermore, others have cautioned that the treatment with manufactured, but biologically similar AMPs possibly could induce microbial resistance to evolutionarily conserved host defense peptides, such as LL-37 (Habets, M. G. and M. A. Brockhurst, Therapeutic antimicrobial peptides may compromise natural immunity. Biol Lett, 2012. 8(3): p. 416-8).

Moreover, an increasing antimicrobial resistance to conventional antibiotics threatens an effective prevention and treatment of microbial infections. Thus, there is a need for identifying new and safe drugs that can be used in the treatment of microbial infections, such as bacterial infections.

SUMMARY OF INVENTION

A main object of the present invention is to provide an antimicrobial agent that can be used in the treatment of antimicrobial infections. The present invention provides a positively charged co-polymer that can be used as an antimicrobial agent.

In one aspect the present invention relates positively charged co-polymers for use as an antimicrobial agent, wherein said positively charged co-polymers consist of amino acids and/or derivatives thereof randomly polymerized into a polypeptide, and wherein at least 75 molar percent of said amino acids are selected from the group consisting of alanine, lysine, glutamate, arginine and tyrosine and/or derivatives thereof.

In a preferred embodiment at least 75 molar percent of said amino acids are selected from the group consisting of alanine, lysine, glutamate and tyrosine and/or derivatives thereof. It is also preferred that the co-polymer has an average positive charge of at least +1. The positively charged co-polymers may also have an average positive charge of at least +2.

As described above, the co-polymer consist of amino acids and/or derivatives thereof randomly polymerized into a polypeptide, and wherein at least 75 molar percent of said amino acids are selected from the group consisting of alanine, lysine, glutamate, arginine and tyrosine and/or derivatives thereof. In one embodiment said alanine is present in a mole fraction in a range of from 0.3 to 0.6. In another embodiment said lysine is present in a mole fraction in a range of from 0.2 to 0.5. Said glutamate may in one embodiment be present in a mole fraction in a range of from 0.05 to 0.3. In an embodiment said tyrosine is present in a mole fraction in a range of from 0.05 to 0.2.

In another embodiment said alanine is present in a mole fraction in a range of from 0.3 to 0.6, said lysine is present in a mole fraction in a range of from 0.2 to 0.5, said lysine is present in a mole fraction in a range of from 0.05 to 3 and/or the said tyrosine is present in a mole fraction in a range of from 0.05 to 0.2. In a specific embodiment the molar ratio of alanine to lysine to glutamate to tyrosine is about 4.6:3.6:1.5:1.

In a particular embodiment the positively charged random co-polymer according to the present invention is a glatiramer acetate co-polymer.

The positively charged random co-polymer as described herein can be used in treating, preventing or ameliorating a microbial infection. Said microbial infection may for example be a bacterial infection. In an embodiment thereof said bacterial infection is a gram-negative bacterial infection. In a particular embodiment said bacterial infection is an *Escherichia coli* infection. The bacterial infection may also be a *Pseudomonas aeruginosa* infection. In another embodiment said bacterial infection is a *Staphylococcus aureus* infection. Thus, in one embodiment the antimicrobial agent is an antibiotic.

Another aspect of the present invention relates to a method for treating, ameliorating or preventing an antimicrobial infection, said method comprising administration of a positively charged random co-polymer to an individual in need thereof, wherein said positively charged random co-polymer is composed of amino acids and wherein 75% of said amino acids are selected from the group consisting of alanine, lysine, glutamate, arginine and tyrosine and derivatives thereof.

It is appreciated that said positively charged random co-polymer is as defined herein and above.

A further aspect of the present invention relates to use of a positively charged random co-polymer in the manufacture of a medicament for the treatment of a microbial infection, wherein said positively charged random co-polymer is composed of amino acids and wherein at least 75% of said amino acids are selected from the group consisting of alanine, lysine, glutamate, arginine and tyrosine and derivatives thereof.

It is appreciated that said positively charged random co-polymer is as defined herein and above.

Yet another aspect of the present invention relates to a composition comprising a positively charged random co-polymer for treating, preventing or ameliorating a microbial infection, wherein said positively charged random co-polymer is composed of amino acids and wherein at least 75% of said amino acids are selected from the group consisting of alanine, lysine, glutamate, arginine and tyrosine and derivatives thereof.

It is appreciated that said positively charged random co-polymer is as defined herein and above.

In one embodiment the composition comprises a pharmaceutically acceptable carrier.

In another embodiment, the composition comprises at least one further active agent. Preferably, said further active agent is an antibiotic. For example, said antibiotic is an aminoglycoside. Preferably, said aminoglycoside is tobramycin. In one embodiment said antibiotic is selected from the group consisting of betalactams, carbepenems, kinolones, macrolides, Vancomycin, Linezolide, daptomycin and sulfur compounds.

In a preferred embodiment said composition is formulated for inhalation.

A further aspect of the present invention relates to a kit of parts comprising the positively charged random co-polymer of the present invention and at least one additive. In one embodiment said additive is an antibiotic. It is preferred that said antibiotic is as defined herein. In another preferred embodiment the positively charged random co-polymer is formulated for an aerosol or a spray.

DESCRIPTION OF DRAWINGS

FIG. 7A illustrates time-lapse microscopy pictures showing bacterial growth at 0, 2, 3 and 4 hours, respectively. GA attained a high killing efficiency in *E. coli*, whereas *S. aureus* demonstrated a lower susceptibility to GA.

FIG. 7B shows bacterial growth curves generated by the oCelloScope segmentation and extraction of surface area (SESA) algorithm. GA exhibited a high antimicrobial activity against *E. coli*, i.e. MIC=31 µg/ml, as opposed to a lower antimicrobial efficacy in *S. aureus*, i.e. MIC=500 µg/ml. All experiments were performed as three replicates.

DETAILED DESCRIPTION OF THE INVENTION

Terms and Definitions

Figure 1:
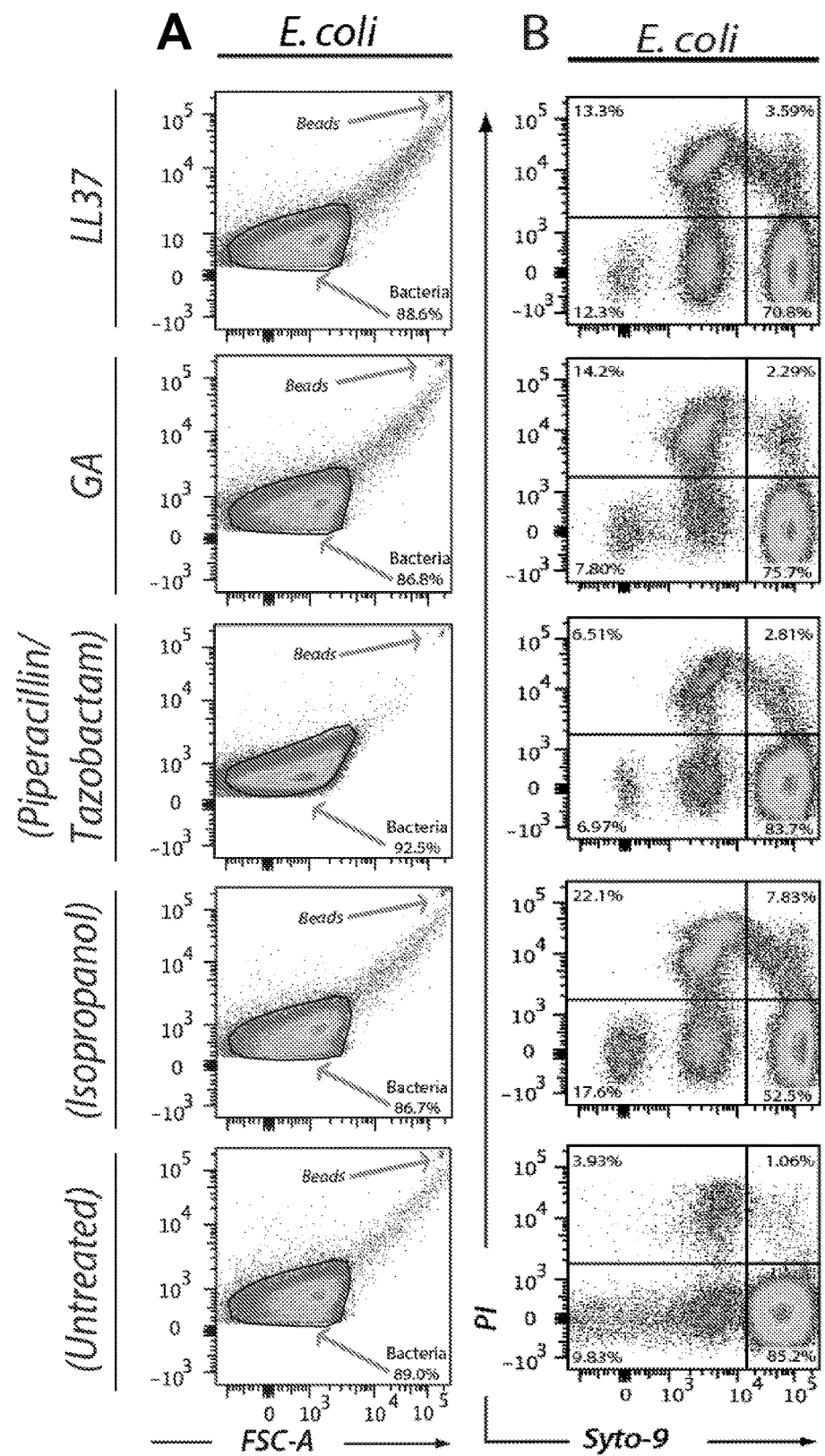
FIG. 1 shows the obtained flow cytometry results on *E. coli*. Flow cytometry was used to determine the antimicrobial activity of GA and LL-37. The flow cytometry diagrams show the results after treatment with 50 µg/ml LL-37, GA, piperacillin/tazobactam, 10% isopropanol and the untreated control. Column A shows the forward-side scatter (FS-SS) and the applied gating strategy. Column B shows a clear distinction between viable, Syto9-positive bacteria (lower right panel of each square), killed bacteria testing positive for PI (upper left panel of each square), and bacteria testing positive for both stains (upper right panel of each square). Bacteria located in lower left panel of each square are membranous remnants of killed bacteria. In columns C and D, the percentage of bacteria testing positive for Syto-9 and PI, respectively, is observed.

To facilitate the understanding of the following description, a number of definitions are presented in the following paragraphs.

The term "treatment", as used anywhere herein comprises any type of therapy, which aims at terminating, preventing, ameliorating and/or reducing the susceptibility to a clinical condition as described herein. In a preferred embodiment, the term treatment relates to prophylactic treatment (i.e. a therapy to reduce the susceptibility of a clinical condition, a disorder or condition as defined herein).

Thus, "treatment," "treating," and the like, as used herein, refer to obtaining a desired pharmacologic and/or physiologic effect, covering any treatment of a pathological and/or clinical condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder or clinical condition from occurring or recurring in a subject, (2) inhibiting the disorder or clinical condition, such as arresting its development, (3) stopping, terminating or alleviating the disorder or clinical condition or at least symptoms associated therewith, so that the host no longer suffers from the disorder or clinical condition or its symptoms, such as causing regression of the disorder or clinical condition or its symptoms, for example, by restoring or repairing a lost, missing or defective function, or stimulating an inefficient process, or (4) relieving, alleviating, or ameliorating the disorder or clinical condition, or symptoms associated therewith, where ameliorating is used in a broad sense to refer to at least a reduction in the magnitude of a parameter, such as inflammation, pain, and/or immune deficiency.

The terms "prevent", "preventing," and "prevention", as used herein, refer to a decrease in the occurrence of symptoms or characteristics of a disorder or clinical condition. The prevention may be complete. The prevention may also be partial, such that for example the occurrence of symptoms or characteristics of a disorder in a subject is less than that which would have occurred without the present invention. Prevention also refers to reduced susceptibility to a clinical condition.

The terms "ameliorate", "ameliorating" and "amelioration", are also used separately herein to refer to a reduction of the severity of the occurrence of symptoms or characteristics of a disorder or clinical condition.

The term "amino acids" as used herein include, but are not limited to the 20 commonly occurring amino acids. Also included are naturally occurring and synthetic derivatives. Amino acids further include amino acid analogs. An "amino acid analog" is chemically related forms of the amino acid having a different configuration, for example, an isomer, D-configuration or L-configuration, or an organic molecule with the approximate size and shape of the amino acid, or an amino acid with derivatives of the atoms that are involved in the peptide bond, so as to be protease resistant when polymerized in a peptide or polypepide.

The terms "amino acid" and "amino acid sequence" as defined herein can include one or more components which are amino acid derivatives and/or amino acid analogs comprising part or the entirety of the residues for any one or more of the 20 naturally occurring amino acids indicated by that sequence. For example, in an amino acid sequence having one or more tyrosine residues, a portion of one or more of those residues can be substituted with homotyrosine. Further, an amino acid sequence having one or more non-peptide or peptidomimetic bonds between two adjacent residues is included within this definition.

The one letter and three letter amino acid codes (and the amino acid that each represents) are as follows: A means ala (alanine); C means cys (cysteine); D means asp (aspartic acid); E means glu (glutamic acid); F means phe (phenylalanine); G means gly (glycine); H means his (histidine); I means ile (isoleucine); K means lys (lysine); L means leu (leucine); M means met (methionine); N means asn (asparagine); P means pro (proline); Q means gln (glutamine); R means arg (arginine); S means ser (serine); T means thr (threonine); V means val (valine); W means trp (tryptophan); and Y means tyr (tyrosine).

The term "positively charged co-polymer" means that the co-polymer as described herein has a positive charge in aqueous solutions at physiological values of pH. It is the positively charged amino acids of the co-polymer that results in the positive charge.

The term "charged amino acid" as defined herein includes positively charged amino acids known in the art. Examples of positively charged amino acids aspartic acid (D, or asp), glutamic acid (E, or glu), histidine (H, or his), arginine (R, or arg) and lysine (K, or lys), which confer a positive (his, lys and arg) or negative (asp and gly) charge at physiological values of pH in aqueous solutions on proteins containing these residues.

Co-Polymer for Use as an Antimicrobial Agent

An increasing antimicrobial resistance to conventional antimicrobial agents and antibiotics threatens an effective prevention and treatment of microbial infections. Thus, there is a need for identifying new and safe drugs that can be used in the treatment of microbial infections, such as bacterial infections.

It is an object of the present invention to provide a safe drug that can be used for the treatment of microbial infections.

One aspect of the present invention relates to a positively charged random co-polymer for use as an antimicrobial agent, wherein said positively charged co-polymer is composed of amino acids and/or derivatives thereof and wherein at least 75 molar percent of said amino acids are selected from the group consisting of alanine, lysine, glutamate, arginine and tyrosine and/or derivatives thereof.

The term "random co-polymer" as used herein refers to a polymer that is composed of amino acids and wherein the amino acid sequence is random. Thus, the co-polymers consist of amino acids and/or derivatives thereof randomly polymerized into a polypeptide. Hence, the co-polymers do not have a specific amino acid sequence. In the present invention, at least 75 molar percent of the amino acids of the co-polymer are selected from the group consisting of alanine, lysine, glutamate, arginine and tyrosine. Thus, the co-polymers can be synthesised by random polymerization of amino acids, wherein 75 molar percent of said amino acids are selected from the group consisting of alanine, lysine, glutamate, arginine and tyrosine. The co-polymers may for example be synthesised by random polymerization of acetic anhydrides of the amino acids. The term "random co-polymer" as used herein may be used interchangeably with the term "co-polymer".

The skilled person can readily substitute structurally-related and/or charge-related amino acids without deviating from the essence of the invention. Thus, the present invention further contemplates conservative amino acid substitutions for tyrosine, glutamate, alanine, arginine and lysine in the present polypeptides. Such conservative substitutions are structurally-related amino acid substitutions, including those amino acids which have about the same charge, hydrophobicity and size as tyrosine, glutamate, alanine or lysine. For example, lysine is structurally-related to arginine and histidine; glutamic acid is structurally-related to aspartic acid; tyrosine is structurally-related to serine, threonine, phenylalanine and tryptophan; and alanine is structurally-related to valine, leucine and isoleucine. These and other conservative substitutions, such as structurally-related synthetic amino acids, are contemplated by the present invention.

The co-polymer of the present invention is composed of amino acids and/or derivatives thereof, wherein in one embodiment at least 75 molar percent, such as at least 80 molar percent, such as for example at least 85 molar percent, such as at least 90 molar percent, such as at least 91 molar percent, such as for example at least 92 molar percent, such as at least 93 molar percent, such as for example at least 94 molar percent, such as at least 95 molar percent, such as for example at least 96 molar percent, such as at least 97 molar percent, such as for example at least 98 molar percent or such as at least 99 molar percent of said amino acids are selected from the group consisting of alanine, lysine, glutamate, arginine and tyrosine and/or derivatives thereof.

In a specific embodiment of the present invention the co-polymer of the present invention is composed of amino acids selected from the group consisting of alanine, lysine, glutamate, arginine and tyrosine and/or derivatives thereof. In a particular embodiment of the present invention the co-polymer of the present invention is composed of amino acids selected from the group consisting of alanine, lysine, glutamate, arginine and tyrosine.

In a more preferred embodiment at least 75 molar percent of the amino acids are selected from the group consisting of alanine, lysine, glutamate and tyrosine and/or derivatives thereof. In a further embodiment at least at least 80 molar percent, such as for example at least 85 molar percent, such as at least 90 molar percent, such as at least 91 molar percent, such as for example at least 92 molar percent, such as at least 93 molar percent, such as for example at least 94 molar percent, such as at least 95 molar percent, such as for example at least 96 molar percent, such as at least 97 molar percent, such as for example at least 98 molar percent or such as at least 99 molar percent of said amino acids are selected from the group consisting of alanine, lysine, glutamate and tyrosine and/or derivatives thereof.

In a specific embodiment of the present invention the co-polymer of the present invention is composed of amino acids selected from the group consisting of alanine, lysine, glutamate and tyrosine and/or derivatives thereof. In a particular embodiment of the present invention the co-polymer of the present invention is composed of amino acids selected from the group consisting of alanine, lysine, glutamate and tyrosine.

In one embodiment of the present invention said alanine is present in a mole fraction in a range of from 0.1 to 0.8, such as from 0.1 to 0.7, such as for example from 0.1 to 0.6, such as from 0.1 to 0.5, such as for example from 0.1 to 0.4, such as from 0.1 to 0.3, or such as for example from 0.1 to 0.2. In another embodiment said alanine is present in a mole fraction in a range of from 0.2 to 0.8, such as from 0.2 to 0.7, such as for example from 0.2 to 0.6, such as from 0.2 to 0.5, such as for example from 0.2 to 0.4 or such as from 0.2 to 0.3. In yet another embodiment said alanine is present in a mole fraction in a range of from 0.3 to 0.8, such as from 0.3 to 0.7, such as for example from 0.3 to 0.6, such as from 0.3 to 0.5 or such as for example from 0.3 to 0.4. In a preferred embodiment said alanine is present in a mole fraction in a range of from 0.3 to 0.6, or more specific in the range of from 0.4 to 0.5. An alanine mole fraction of for example 0.3 means that 30 percent of the amino acids of the co-polymer are alanine residues.

In one embodiment of the present invention said lysine is present in a mole fraction in a range of from 0.1 to 0.8, such as from 0.1 to 0.7, such as for example from 0.1 to 0.6, such as from 0.1 to 0.5, such as for example from 0.1 to 0.4, such as from 0.1 to 0.3, or such as for example from 0.1 to 0.2. In another embodiment said lysine is present in a mole fraction in a range of from 0.2 to 0.8, such as from 0.2 to 0.7, such as for example from 0.2 to 0.6, such as from 0.2 to 0.5, such as for example from 0.2 to 0.4 or such as from 0.2 to 0.3. In yet another embodiment said lysine is present in a mole fraction in a range of from 0.3 to 0.8, such as from 0.3 to 0.7, such as for example from 0.3 to 0.6, such as from 0.3 to 0.5 or such as for example from 0.3 to 0.4. In a preferred embodiment said lysine is present in a mole fraction in a range of from 0.2 to 0.5, or more specific in the range of from 0.3 to 0.4.

In one embodiment of the present invention said glutamate is present in a mole fraction in a range of from 0.1 to 0.8, such as from 0.1 to 0.7, such as for example from 0.1 to 0.6, such as from 0.1 to 0.5, such as for example from 0.1 to 0.4, such as from 0.1 to 0.3, or such as for example from 0.1 to 0.2. In another embodiment said glutamate is present in a mole fraction in a range of from 0.2 to 0.8, such as from 0.2 to 0.7, such as for example from 0.2 to 0.6, such as from 0.2 to 0.5, such as for example from 0.2 to 0.4 or such as from 0.2 to 0.3. In yet another embodiment said glutamate is present in a mole fraction in a range of from 0.3 to 0.8, such as from 0.3 to 0.7, such as for example from 0.3 to 0.6, such as from 0.3 to 0.5 or such as for example from 0.3 to 0.4.

In a preferred embodiment said glutamate is present in a mole fraction in a range of from 0.05 to 0.3, or more specific in the range of from 0.1 to 0.2.

In one embodiment of the present invention said tyrosine is present in a mole fraction in a range of from 0.1 to 0.8, such as from 0.1 to 0.7, such as for example from 0.1 to 0.6, such as from 0.1 to 0.5, such as for example from 0.1 to 0.4, such as from 0.1 to 0.3, or such as for example from 0.1 to 0.2. In another embodiment said tyrosine is present in a mole fraction in a range of from 0.2 to 0.8, such as from 0.2 to 0.7, such as for example from 0.2 to 0.6, such as from 0.2 to 0.5, such as for example from 0.2 to 0.4 or such as from 0.2 to 0.3. In yet another embodiment said tyrosine is present in a mole fraction in a range of from 0.3 to 0.8, such as from 0.3 to 0.7, such as for example from 0.3 to 0.6, such as from 0.3 to 0.5 or such as for example from 0.3 to 0.4. In a preferred embodiment said tyrosine is present in a mole fraction in a range of from 0.05 to 0.2, or more specific in the range of from 0.05 to 0.15.

Thus, a preferred embodiment of the present invention relates to a co-polymer wherein said alanine is present in a mole fraction in a range of from 0.3 to 0.6, said lysine is present in a mole fraction in a range of from 0.2 to 0.5, said lysine is present in a mole fraction in a range of from 0.05 to 3 and/or the said tyrosine is present in a mole fraction in a range of from 0.05 to 0.2.

A particular embodiment of the present invention relates to a co-polymer wherein said alanine is present in a mole fraction in a range of from 0.4 to 0.5, said lysine is present in a mole fraction in a range of from 0.3 to 0.4, said lysine is present in a mole fraction in a range of from 0.1 to 0.2 and/or the said tyrosine is present in a mole fraction in a range of from 0.05 to 0.15.

In another embodiment of the present invention the molar ratio of alanine to lysine to glutamate to tyrosine is from 1:1:1:1 to 6:5:4:1, such as from 1:1:1:1 to 5:4:3:1, or such as for example from 1:1:1:1 to 4:3:2:1 or such as from 1:1:1:1 to 3:2:2:1. In a preferred embodiment the molar ratio of alanine to lysine to glutamate to tyrosine is from 4:3:1:1 to 5:4:2:1. In a specific embodiment the molar ratio of alanine to lysine to glutamate to tyrosine is about 4.6:3.6:1.5:1. A molar ratio of alanine to lysine to glutamate to tyrosine of 1:1:1:1 means that the molar amounts of alanine, lysine, glutamate and tyrosine, respectively, are the same. A molar ratio of alanine to lysine to glutamate to tyrosine of for example 6:5:4:1 means that molar amount of alanine is 6 times the molar amount of tyrosine, the molar amount of lysine is 5 times the molar amount of tyrosine and the molar amount of glutamate is 4 times the molar amount of tyrosine.

The copolymer of the present invention is positively charged. In a preferred embodiment the co-polymer has a net positive charge of at least +1. In another preferred embodiment the co-polymer has a net positive charge of at least +2. The co-polymer may also have a net positive charge of at least +3 or such as at least +4, at least +5, such as at least +6, such as for example at least +7, at least +8, such as at least +9 or for example at least +10

In on embodiment the co-polymer comprises at least two positively charged amino acid residues, such as at least three positively charged amino acid residues, at least 4 positively charged amino acid residues or at least 5 positively charged amino acid residues.

In another embodiment of the present invention the co-polymer comprises positively charged amino acid residues being present in a mole fraction in a range of from 0.02 to 0.2, such as in a range of from 0.02 to 0.1, such as for example in a range of from 0.02 to 0.08, such as in a range of from 0.02 to 0.1, such as for example in a range of from 0.02 to 0.08, such as in a range of from 0.02 to 0.06, such as for example in a range of from 0.02 to 0.04.

In a more specific embodiment the co-polymer has an average length of about 50 amino acid residues and comprises at least two positively charged amino acid residues, such as at least three positively charged amino acid residues, at least 4 positively charged amino acid residues or at least 5 positively charged amino acid residues.

In one embodiment of the present invention the co-polymer is composed of at least 10 amino acid residues, such as at least 15 amino acid residues, such as for example at least 20 amino acid residues, such as at least 25 amino acid residues, such as for example at least 30 amino acid residues, such as at least 35 amino acid residues, such as for example at least 40 amino acid residues, such as at least 45 amino acid residues, such as for example at least 50 amino acid residues, such as at least 60 amino acid residues or such as for example at least 70 amino acid residues, such as at least 80 amino acid residues.

In a preferred embodiment the co-polymer is composed of at least 50 amino acid residues.

In one embodiment the co-polymer has an average length of about 20 amino acid residues such as about 25 amino acid residues, such as for example about 30 amino acid residues, such as about 35 amino acid residues, such as for example about 40 amino acid residues, such as about 45 amino acid residues, such as for example about 50 amino acid residues, such as about 60 amino acid residues, such as for example about 70 amino acid residues, such as about 80 amino acid residues, such as for example about 90 amino acid residues or such as about 100 amino acid residues. It is preferred that the co-polymers have an average length of about 50 amino acid residues.

The co-polymers according to the present invention may be prepared by methods known in the art, for example, the process disclosed in U.S. Pat. No. 3,849,550, wherein the N-carboxyanhydrides of tyrosine, alanine, y-benzyl glutamate and E-N-trifluoro-acetyllysine are polymerised at ambient temperature in anhydrous dioxane with diethylamine as initiator.

In a preferred embodiment the co-polymer of the present invention is a glatiramer acetate co-polymer.

Glatiramer acetate is also known as Copolymer 1, Cop-1, or Copaxone™. It is known as an immunomodulatory drug, and is applied as a drug for treatment of multiple sclerosis (U.S. Pat. No. 3,849,550). Glatiramer acetate is co-polymers that are obtained by random polymerization of acetic anhydrides of the amino acids lysine, glutamate, alanine and tyrosine. The co-polymers have an average length of 50 amino acid residues.

Microbial Infection

The present invention relates to a positively charged random co-polymer for use as an antimicrobial agent. The term "antimicrobial agent" as used herein refers to an agent that either kills or inhibits the growth of a microorganism or has a lytic activity against microorganisms. The term "microorganism" as used herein refers to a microscopic organism or microbe. "Microorganisms" as referred to herein include bacteria, archaea, protozoa, fungus, helminths and vira. In a preferred embodiment the microorganism is selected from the group consisting of vira and bacteria. It is preferred that the vira is enveloped vira, i.e. the virus has an envelope. In a more preferred embodiment the microorganism is a bacterium. In a most preferred embodiment the microorganism is a gram-negative bacterium.

In a preferred embodiment the antimicrobial agent is an antibiotic. The term "antibiotic" as used herein refers to an agent that either kills or inhibits the growth of a bacteria, archaea and/or protozoa.

A preferred embodiment of the present invention relates to positively charged co-polymer as described herein for use in treating, preventing or ameliorating a microbial infection.

In one embodiment, the microbial infection is a fungal infection. A fungal infection is an infection caused by a fungus. The term "microorganism" is defined above. Fungus may for example be selected from the group consisting of *Candida, Aspergillus, Nocardia* and *Pneumocystis*.

In another embodiment the microbial infection is a protozoan infection. A protozoan infection is an infection caused by protozoa. Protozoa may for example be selected from the group consisting of *Plasmodia, Leishmania, Trypanosoma* and *Entamoeba*.

In a further embodiment the microbial infection is a helminth infection. A helminth infection is an infection caused by a helminth. Helminth may for example be selected from the group consisting of Nematodes, cestodes and trematodes.

In one embodiment the microbial infection is a viral infection. It is preferred that the viral infection is caused by enveloped viruses.

In a preferred embodiment the microbial infection is a bacterial infection. The bacterial infection may be either a gram positive bacterial infection or a gram negative bacterial infection, i.e. the bacterial infection may be caused by either gram positive bacteria or gram negative bacteria. Gram positive bacteria may for example be selected from the group consisting of *Actinomyces, Bacillus, Clostridium, Corynebacterium, Enterococcus, Gardnerella, Lactobacillus, Listeria, Mycobacterium, Mycoplasma, Nocardia, Propionibacterium, Staphylococcus* and *Streptococcus*.

In a specific embodiment the bacterial infection is a *Staphylococcus aureus* infection.

In a preferred embodiment the bacterial infection is a gram negative bacterial infection. Thus, in one embodiment the bacterial infection is caused by gram negative bacteria, wherein said gram negative bacteria are selected from the group consisting of *Bortadella, Burkholderia, Campylobacter, Chlamydia, Enterobacter, Escherichia, Fusobacterium, Helicobacter, Hemophilus, Klebsiella, Legionella, Leptospiria, Neisseria, Nitrobacter, Proteus, Pseudomonas, Rickettsia, Salmonella, Serratia, Shigella, Thiobacter, Treponema, Vibrio* and *Yersinia*

In a specific embodiment the bacterial infection is an *Escherichia coli* infection. In another specific embodiment the bacterial infection is a *Pseudomonas aeruginosa* infection. In another specific embodiment the bacterial infection is a *Burkholderia cepacia* infection.

Treatment

The co-polymer of the present invention can be used in the treatment of microbial infections. Microbial infections are defined above.

Thus, another aspect of the present invention relates to a method for treating, preventing or ameliorating an antimicrobial infection, said method comprising administration of positively charged random co-polymers to an individual in need thereof, wherein said positively charged random co-polymers are composed of amino acids and wherein 75% of said amino acids are selected from the group consisting of alanine, lysine, glutamate, arginine and tyrosine.

The positively charged random co-polymers are as defined herein and above. Also, microbial infections are as defined herein and above. Thus, in a preferred embodiment the microbial infection is a bacterial infection.

Microbial infections may in one embodiment include septicaemia with bacteria in the blood, pneumonia, sinusitis, cystitis. In the treatment of these infections, the co-polymers will preferably be administered by the intravenous route.

The microbial infection may also be a central nervous system infection such as for example meningitis and encephalitis. Thus in one embodiment the co-polymer of the present invention can be used in the treatment of meningitis and/or encephalitis.

Chronic ulcers on the legs are a common complication to venous insufficiency. These ulcers heal poorly and are colonized with a multi-bacterial flora consisting of both gram negative and gram positive bacteria. In this situation the co-polymer can be administered topically into the ulcers. Thus, in one embodiment the co-polymer of the present invention can be used in the treatment of ulcers such as for example chronic ulcers or more specific, chronic ulcers on the legs.

The method for treating, preventing or ameliorating a microbial infection may also involve an additional agent suitable for treating, preventing or ameliorating a microbial infection such as antimicrobial agents or antibiotics. Thus, in one embodiment the method for treatment further comprises a step of administering an additional antimicrobial agent or antibiotic.

Antimicrobial agents against bacteria may for example be selected from the group consisting of betalactams, carbepenems, kinolones (for instance ciprofloxacin), macrolides (for instance clarithromycin), Vancomycin, Linezolide, daptomycin and sulfur compounds. Sulfur compounds are preferably used in combination with folate inhibitors like for instance trimethoprim. The betalactam may for example be selected from the group consisting of penicillin, penicillin derivatives, cephalosporins, monobactams, and carbapenems. Monobactam may for example include aztreonam.

The additional agent may also include beta lactamase inhibitors such as for example tazobactam.

It is also an object of the present invention to provide use of positively charged random co-polymers for the manufacture of a medicament for the treating, preventing or ameliorating a microbial infection, wherein said positively charged co-polymer is composed of amino acids and wherein 75% of said amino acids are selected from the group consisting of alanine, lysine, glutamate, arginine and tyrosine and derivatives thereof.

Embodiments of the positively charged random co-polymers are as defined herein and above.

Pharmaceutical Formulations

The co-polymer according to the present invention is used as an antimicrobial agent or for treating, ameliorating and/or preventing an antimicrobial infection. Thus, it is preferred that the co-polymers, compositions or formulations as described herein are pharmaceutically acceptable. In one embodiment the co-polymer as described herein is in the form of a pharmaceutical formulation.

Accordingly, the present invention further provides a pharmaceutical formulation, which comprises a co-polymer as defined herein and a pharmaceutically acceptable salt or a salt or tautomer thereof, as herein defined, and a pharmaceutically acceptable carrier. Thus, in one embodiment the co-polymer of the present invention further comprises a pharmaceutically acceptable carrier. The pharmaceutical formulations may be prepared by conventional techniques, e.g. as described in Remington: The Science and Practice of Pharmacy 2005, Lippincott, Williams & Wilkins.

The pharmaceutically acceptable carriers can be either solid or liquid. Solid form preparations include powders, tablets, pills, capsules, cachets, suppositories, and dispersible granules. A solid carrier can be one or more excipients which may also act as diluents, flavoring agents, solubilizers, lubricants, suspending agents, binders, preservatives, wetting agents, tablet disintegrating agents, or an encapsulating material.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The co-polymer of the present invention may be formulated for parenteral administration and may be presented in unit dose form in ampoules, pre-filled syringes, small volume infusion or in multi-dose containers, optionally with an added preservative. The co-polymer may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

In a preferred embodiment the co-polymer of the present invention is formulated for oral administration. Oral administration forms include solid form preparations including powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifice, chewing gum, or solid form preparations which are intended to be converted shortly before use to liquid form preparations, such as solutions, suspensions, and emulsions. In powders, the carrier is a finely divided solid which is a mixture with the finely divided active component.

In a preferred embodiment the co-polymer as described herein is formulated in a tablet or capsule. In tablets, the active component is mixed with the carrier having the necessary binding capacity in suitable proportions and compacted in the shape and size desired. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. Suitable solvents for the preparation of an oily solution include glycerol, diluted alcohol and propylene glycol.

Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well-known suspending agents.

The co-polymer of the present invention may also be formulated in a wide variety of formulations for parenteral administration.

For injections and infusions the formulations may take such forms as suspensions, solutions, or emulsions in oily or aqueous vehicles, for example solutions in aqueous polyethylene glycol. Alternatively, the co-polymer may be in powder form, obtained by aseptic isolation of sterile solid or by lyophilisation from solution for constitution before use with a suitable vehicle, e.g., sterile, pyrogen-free water. The formulations can be presented in unit-dose or multi-dose sealed containers, such as ampoules, vials, pre-filled syringes, infusion bags, or can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Examples of oily or non-aqueous carriers, diluents, solvents or vehicles include propylene glycol, polyethylene glycol, vegetable oils, and injectable organic esters, and may contain formulatory agents such as preserving, wetting, emulsifying or suspending, stabilizing and/or dispersing agents.

The formulations for injection will typically contain from about 0.5 to about 25% by weight of the active ingredient in solution.

Topical Delivery

The co-polymer may also be administered topically. Regions for topical administration include the skin surface and also mucous membrane tissues of the vagina, rectum, nose, mouth, and throat.

A topical composition comprising the co-polymer of the present invetion will typically include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The co-polymers of the present invention may be formulated for topical administration to the epidermis as ointments, creams or lotions, or as a transdermal patch. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin or a fatty acid. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention also include those suitable for application to the eye. An eye lotion may comprise a sterile aqueous solution optionally containing a bactericide.

Nasal, Pulmonary and Bronchial Administration

Formulations for use in nasal, pulmonary and/or bronchial administration are normally administered as aerosols in order to ensure that the aerosolized dose actually reaches the mucous membranes of the nasal passages, bronchial tract or the lung. The term "aerosol particle" is used herein to describe the liquid or solid particle suitable for nasal, bronchial or pulmonary administration, i.e., that will reach the mucous membranes.

Typically aerosols are administered by use of a mechanical devices designed for pulmonary and/or bronchial delivery, including but not limited to nebulizers, metered dose inhalers, and powder inhalers. With regard to construction of the delivery device, any form of aerosolization known in the art, including but not limited to spray bottles, nebulization, atomization or pump aerosolization of a liquid formulation, and aerosolization of a dry powder formulation, can be used.

Liquid Aerosol Formulations in general contain a co-polymer of the present invention in a pharmaceutically acceptable diluent. Pharmaceutically acceptable diluents include but are not limited to sterile water, saline, buffered saline, dextrose solution, and the like.

Formulations for dispensing from a powder inhaler device will normally comprise a finely divided dry powder containing pharmaceutical composition of the present invention (or derivative) and may also include a bulking agent, such as lactose, sorbitol, sucrose, or mannitol in amounts which facilitate dispersal of the powder from the device. Dry powder formulations for inhalation may also be formulated using powder-filled capsules, in particularly capsules the material of which is selected from among the synthetic plastics.

The formulation is formulated to the type of device employed and may involve the use of an appropriate propellant material, in addition to the usual diluents, adjuvants and/or carriers useful in therapy and known to the person skilled in the art. The propellant may be any propellant generally used in the art. Specific non-limiting examples of such useful propellants are a chlorofluorocarbon, a hydrofluorocarbon, a hydrochlorofluorocarbon, or a hydrocarbon.

The formulations of the present embodiment may also include other agents useful for pH maintenance, solution stabilization, or for the regulation of osmotic pressure.

The formulations of the present embodiment may also include other agents useful for pH maintenance, solution stabilization, or for the regulation of osmotic pressure.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel. For example, a simple adhesive patch can be prepared from a backing material and an acrylate adhesive.

Administration

The co-polymers or compositions provided herein may be administered by any suitable method available in the art. The main routes of administration are parenteral injections, inhalations and direct applications to wounds and ulcers as will be described below. Other drug-administration methods, such as subcutaneous injection, which is effective to deliver the drug to a target site or to introduce the drug into the bloodstream, are also contemplated. Furthermore, oral administration, intranasal administration and administration by pulmonary inhalation is convenient and effective methods of administration, which could be used.

The co-polymers or compositions of the present invention are preferably administered orally, for example as an oral tablet or capsule or a liquid extract. This is a convenient non-invasive approach for administration, which is also preferred by most patients. The co-polymers or compositions are easily taken up via the gastrointestinal tract.

However, co-polymers or compositions of the invention may also be administered parenterally. This could particularly be relevant, where the co-polymers or compositions are administered in combination with an additional agent, which requires parenteral injection. Thus, in one embodiment of the present invention, the co-polymers or compositions provided herein are administered parenterally, that is by intravenous, intramuscular, subcutaneous, intranasal, intrarectal, intravaginal or intraperitoneal administration. The subcutaneous and intramuscular forms of parenteral administration are generally preferred. Appropriate dosage forms for such administration may be prepared by conventional techniques. The co-polymers or compositions may also be administered by inhalation that is by intranasal and oral inhalation administration. In a preferred embodiment, the co-polymers or compositions of the present invention are delivered by intravenous, subcutaneous, and/or intra-muscular administration.

The co-polymers or compositions according to the invention may be administered with at least one other compound. The co-polymers or compositions may be administered simultaneously, either as separate formulations or combined in a unit dosage form, or administered sequentially.

Dosages

The dosage requirements will vary with the particular composition employed, the route of administration and the particular individual being treated. Ideally, an individual to be treated by the present method will receive a pharmaceutically effective amount of the co-polymers or compositions in the maximum tolerated dose, generally no higher than that required before drug resistance develops.

The methods and uses of the present invention provide that the co-polymers or a derivative thereof is administered in an effective amount. By "effective amount" herein is meant a dose that produces the therapeutic effects for which it is administered. The exact dose will depend on the clinical condition or disorder to be treated, and can be ascertained by one skilled in the art using known techniques. For example, the co-polymers or compositions of the present invention can be administered to a person in an amount of from 1 µg/kg to about 100 mg/kg per day. In addition, as is known in the art, adjustments for age as well as the body weight, general health, sex, diet, time of administration, drug interaction, the route and form of administration, and the severity of the clinical condition (e.g. decreased kidney and liver function) may be necessary, and will be ascertainable with routine experimentation by those skilled in the art.

Co-polymers or compositions or a derivative can be administered in dosage ranges of 5 µg to about 20 g per day. In one embodiment, suitable dosage ranges of co-polymers or a derivative thereof are typically 1-500 mg daily, preferably 1-100 mg daily and more preferably 1-40 mg daily, 1-30 mg daily, 10-30 mg daily, 15-25 mg daily or about 20 mg daily.

In one embodiment the co-polymer as described herein is to be administered in a dosage of from 1 µg/kg-10,000 µg/kg body weight, such as 1 µg/kg-7,500 µg/kg, such as 1 µg/kg-5,000 µg/kg, such as 1 µg/kg-2,000 µg/kg, such as 1 µg/kg-1,000 µg/kg, such as 1 µg/kg-700 µg/kg, such as 5 µg/kg-500 µg/kg, such as 10 µg/kg to 100 µg/kg bodyweight.

In another embodiment the co-polymer as described herein is to be administered in a dosage of from 1 µg/kg-1,000 µg/kg body weight, such as 1 µg/kg-500 µg/kg, such as 1 µg/kg-250 µg/kg, such as 1 µg/kg-100 µg/kg, such as 1 µg/kg-50 µg/kg, such as 1 µg/kg to 10 µg/kg bodyweight.

In yet another embodiment the co-polymer as described herein is to be administered in a dosage of from 10 µg/kg-10,000 µg/kg body weight, such as 10 µg/kg-7,500 µg/kg, such as 10 µg/kg-5,000 µg/kg, such as 10 µg/kg-2,000 µg/kg, such as 10 µg/kg-1,000 µg/kg, such as 10 µg/kg-700 µg/kg, such as 10 µg/kg-500 µg/kg, such as 10 µg/kg to 100 µg/kg bodyweight.

The co-polymers including a derivative thereof as defined elsewhere herein is preferably administered at least once daily, and may therefore be administered once or twice daily or three times daily.

Target Group

The present invention provides methods and uses, which involves administering an effective amount of co-polymer or a derivative thereof to an individual in need thereof.

Generally, "an individual in need thereof" is an individual, who suffers from a microbial infection or in particular a bacterial infection.

An individual in need thereof thus includes any individual having any type of microbial infection, in particular a bacterial infection. In other words, the methods, uses, co-polymers and compositions as described herein are applicable to any individual having a microbial infection. The individual may be any animal or human. In a preferred embodiment the individual is a person or a human.

Composition

The present invention provides a composition comprising the co-polymer of the present invention. The composition may for example be a pharmaceutical composition. As used herein, "pharmaceutical" will be understood to encompass both human and animal pharmaceuticals.

Thus, another aspect of the present invention relates to a composition comprising a positively charged co-polymer for treating, preventing or ameliorating a microbial infection, wherein said positively charged co-polymer is composed of amino acids and wherein 75% of said amino acids are selected from the group consisting of alanine, lysine, glutamate, arginine and tyrosine and derivatives thereof.

The positively charged co-polymer of the composition is as defined elsewhere herein.

The composition may also comprise a pharmaceutically acceptable carrier. The term "pharmaceutically acceptable carrier" refers to a vehicle which delivers the active components to the intended target and which does not cause harm to humans or other recipient organisms. Useful carriers include, for example, water, acetone, ethanol, ethylene glycol, propylene glycol, butane-1,3-diol, isopropyl myristate, isopropyl palmitate, or mineral oil. The composition may be formulated in any form appropriate to the mode of administration, for example, solutions, colloidal dispersions, emulsions (oil-in-water or water-in-oil), suspensions, creams, lotions, gels, foams, sprays, aerosol, ointment, tablets, suppositories, and the like. It is appreciated that the composition is formulated as described in the section "Pharmaceutical formulations". In a preferred embodiment the composition is formulated for an aerosol or a spray.

Methodology and components for formulation of compositions are well known, and can be found, for example, in Remington's Pharmaceutical Sciences, Eighteenth Edition, A. R. Gennaro, Ed., Mack Publishing Co. Easton Pa., 1990.

Kit of Parts

The present invention also provides a kit of parts comprising the positively charged random co-polymer of the present invention and additives such as for example antibiotics or antimicrobial agents used in combination with the co-polymer.

A further aspect of the present invention relates to a kit of parts comprising the positively charged random co-polymer of the present invention and at least one additive. Preferably, said additive is an antimicrobial agent. The antimicrobial agent or the antibiotic is as defined herein above.

In one embodiment the kit of parts comprises a composition comprising the positively charged random co-polymer of the present invention and at least one additive. The composition is as defined herein above. In a preferred embodiment the composition or the positively charged co-polymer of the present invention is formulated for an aerosol or a spray. Thus, in one embodiment the kit comprises an aerosol or a spray comprising the positively charged co-polymer of the present invention. Preferably, the additive is an antimicrobial agent. The antimicrobial agent is as defined herein above.

The additive may also be compounds used in the compositions or formulations as described herein.

EXAMPLES

Materials and Methods

Antimicrobial Susceptibility Testing by Flow Cytometry-Based Assay

*E. coli* (strain NCTC 10418), *P. aeruginosa* (Strain PAO1) and *S. aureus* (Wood 46, NCTC 7121) cells were grown in 5 mL of Todd Hewitt Broth medium (THB; Sigma-Aldrich). Bacteria were cultivated at 37° C. for 15 h in a 15 mL tube to obtain late-log phase cultures. Bacterial cultures were pelleted at 3096 g for 10 minutes; the supernatant was discarded and bacteria were resuspended in phosphate-buffered saline (PBS) supplemented with 40 mg/ml human albumin to mimic chemical properties of blood. Bacteria were diluted to a standardized inoculum of $10^9$ CFU/mL.

Bacteria were treated with GA, LL-37, Piperacillin/Tazobactam or Vancomycin in varying concentrations, i.e. 50, 25, 10 or 2 µg/ml, for 30 minutes. As a positive control, bacteria were treated with 7% isopropanol. Hereafter, bacteria were pelleted at 3096 g for 10 minutes; the supernatant was discarded and bacteria were resuspended in PBS. The antimicrobial effect was tested in a well-established and widely used flow cytometry-based assay (LIVE/DEAD® BacLight™ Bacterial Viability and Counting Kit (L34856), Molecular Probes/Invitrogen) according to manufacturer's manual.

For each bacteria, the flow cytometry-based assay was repeated four times.

Piperacillin/Tazobactam is a combination antibiotic containing the extended-spectrum antibiotic piperacillin, an antibiotic of the ureidopenicillin class, and the β-lactamase inhibitor tazobactam. The combination has activity against many Gram-positive and Gram-negative bacteria. Vancomycin is an antibiotic of the glycopeptide class and is effective mostly against Gram-positive bacteria.

Antimicrobial Susceptibility Testing by the CelloScope System

*E. coli* (strain NCTC 10418) and *S. aureus* (Wood 46, NCTC 7121) were grown overnight in Sensititre® cation-adjusted Mueller-Hinton broth with TES (CAMHBT, TREK Diagnostic System). Bacterial cell suspensions were adjusted to 0.5 McFarland standard using a nephelometer. Subsequently, bacteria were diluted in CAMHBT according to the recommended final inoculum size for broth dilution ($5 \times 10^5$ colony-forming units (CFU) $ml^{-1}$) (Wiegand, I., K. Hilpert, and R. E. Hancock, *Agar and broth dilution methods to determine the minimal inhibitory concentration (MIC) of antimicrobial substances*. Nat Protoc, 2008. 3(2): p. 163-75) and analyzed in Nunc Edge 96-well plates by the oCelloScope system.

The oCelloScope is a digital time-lapse microscopy technology that scans through a fluid sample generating series of images as described in 2013 by Fredborg et al. (Fredborg, M., et al., *Real-time optical antimicrobial susceptibility testing*. J Clin Microbiol, 2013. 51(7): p. 2047-53). As a result of the tilted imaging plane, the images recorded by the oCelloScope system constitute a parallelepipedum that forms the image stack. The projected z-stack image of a single z-plane was generated by combining the tilted images. Each well was scanned repeatedly every 15 min for 2 hours and every 10 min for the following 5 hours. The oCelloScope instrument was placed inside an Innova 44 incubator allowing precise temperature regulation. Time-lapse experiments and digital analysis were conducted by a custom automation script in MATLAB and image processing was conducted with ImageJ 1.48 v. Growth kinetics was determined by image stack processing based on contrast based Segmentation and Extraction of Surface Area (SESA). GraphPad Prism version 6.0 g for Mac OS X, was used for statistical analysis. Determination of MIC values for all experiments on QC reference strains was carried out in triplicate experiments. Results were reported when at least two out of three MIC results was in agreement.

Glatiramer Acetate Binds the Microbial Membrane

GA was diluted in freshly made 0.1 M $NaHCO_3$ and labeled with Alexa Fluor 488 according to manufacturer's instruction. Late-log phase *E. coli* (strain NCTC 10418), *P. aeruginosa* (strain PAO1, ATCC 15692) and *S. aureus* (Wood 46, NCTC 7121) were resuspended in PBS or PBS supplemented with 50 mM NaCl; treated with either 50 μg/ml or 10 μg/ml Alexa Fluor® 488-labeled GA and incubated on a shaker at 37° C. for 30 minutes. Hereafter, bacteria were diluted 1:100 in PBS and analyzed on a Novocyte™ flow cytometer.

Colony-Forming Unit (CFU) Counting

Late-log phase *E. coli* (strain NCTC 10418), *P. aeruginosa* (strain PAO1, ATCC 15692) and *S. aureus* (Wood 46, NCTC 7121) were resuspended in PBS and treated with different concentrations of glatiramer acetate (GA) or LL-37 (Innovagen, Lund, Sweden) and incubated on a shaker for 30 minutes at 37° C. Subsequently, a dilution series was performed to achieve a suitable amount of bacteria on the 5% blood agar plates. The 5% blood agar streak plates were cultured at 37° C. for 16 h and the resulting CFUs on the blood agar plates were imaged with a digital camera and counted with the aid of the software ImageJ 1.48v.

Example 1

Antibacterial Effect on *Escherichia coli*

FIG. 1 shows the obtained flow cytometry results on *E. coli*. Flow cytometry was used to determine the antimicrobial activity of GA and LL-37. The flow cytometry diagrams show the results after treatment with 50 μg/ml LL-37, GA, piperacillin/tazobactam, 7% isopropanol and the untreated control. FIG. 1, column A shows the forward-side scatter (FS-SS) and the applied gating strategy. This gating strategy was primarily applied to avoid counting beads in the upper right corner of the FS-SS. However, FS-SS showed no distinction between treated and untreated samples. Thus, a two-color fluorescence assay of bacterial viability, including PI and Syto9 staining, was applied. Syto9 stains all bacteria in a population, i.e. those with intact and those with damaged membranes. In contrast, propidium iodide (PI) penetrates only bacteria with damaged membranes, thereby making quantification of bacterial viability possible.

FIG. 1, column B shows a clear distinction between viable, Syto9-positive bacteria (lower right panel of each square), killed bacteria testing positive for PI (upper left panel of each square), and bacteria testing positive for both stains (upper right panel of each square). Bacteria located in lower left panel of each square are either in an intermediate state before being PI-positive, or membranous remnants of killed bacteria. In contrast, bacteria located in upper right panel of each square are presumably highly affected by the treatment, however, without losing their membranous integrity. The different treatments gave rise to a marked increase of the PI-positive population (upper left panel of each square) and two populations of dimly stained Syto9-positive bacteria (lower left panel of each square). This pattern was most distinctive when treating bacteria with 10% isopropanol, however, bacteria treated with LL-37, GA and piperacillin/tazobactam exhibited a similar profile.

In FIG. 1, columns C and D, the percentage of bacteria testing positive for Syto-9 and PI, respectively, was observed. In the untreated sample, it is observed that 87.2% of the bacteria are testing positive for Syto-9, whereas 5.5% of the untreated bacteria are testing positive for PI. However, it is observed that bacteria treated with GA have a decreased percentage of Syto9-positive bacteria (78.3%) and an increased PI positivity (17.7%). It is the same picture emerging when treating bacteria with LL-37. After treatment with LL-37, 17.8% of the bacteria stains positive for PI, whereas 75.1% of the bacteria stains positive for Syto9. The *E. coli* population treated with the antibiotic piperacillin/tazobactam, shows a lower level of PI positivity (10%). The percentage of Syto9-positive bacteria remains at 86.8%, thereby exhibiting a phenotype similar to the untreated control. In the positive control, which was treated with 7% isopropanol, 61.7% of the bacteria tested positive for Syto-9 and 32.2% tested positive for PI. As observed in column C, treatment of bacteria seemed to involve an increasing percentage of dimly stained syto9-positive bacteria.

Example 2

Antibacterial Effect on *Pseudomonas aeruginosa*

The antibacterial effect of GA on the gram-negative strain *P. aeruginosa* was tested by carrying out an experiment as described in Example 1. As observed in FIG. 2, the Gram-negative *P. aeruginosa* was highly susceptible to GA, when compared to *E. coli*. Although the untreated control stained positive for PI, this seemed to be explained by the capability of intact *P. aeruginosa* to secrete large quantities of DNA to the extracellular milieu. Interestingly, both LL-37 and GA were capable of killing more than 40% of the bacteria as when compared to the untreated control.

Piperacillin/tazobactam reached higher efficacy, i.e. about 30% PI positivity, than observed for *E. coli*, but lower than when comparing with LL-37 and GA in both strains. Strikingly, both GA and LL-37 were more potent than when treating bacteria with 7% isopropanol.

Example 3

Antibacterial Effect on *Staphylococcus aureus*

Figure 3:
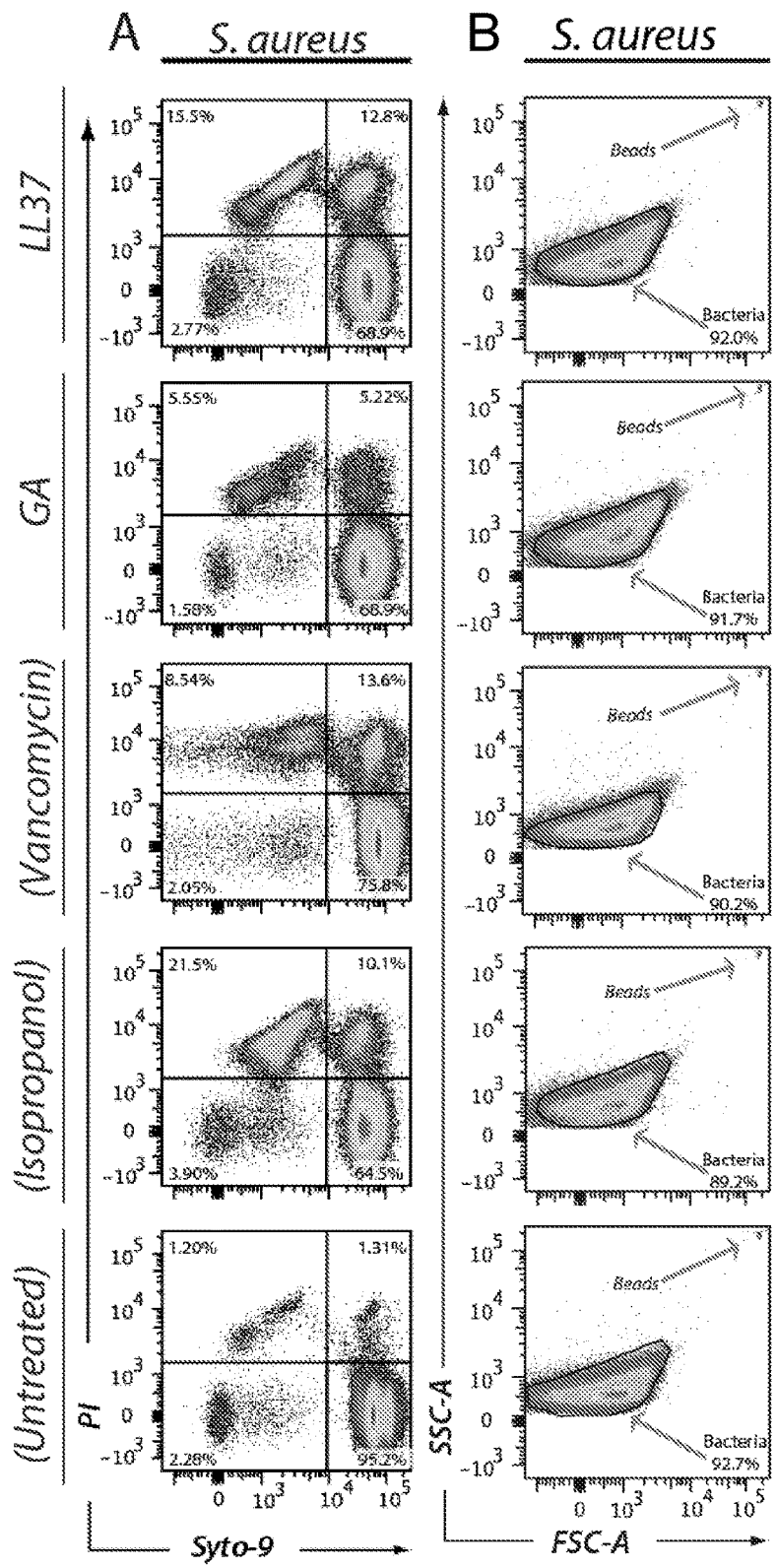
FIG. 3 depicts the obtained flow cytometry results on *S. aureus*. In the untreated sample, 96.5% of the bacteria were viable (testing positive for Syto-9), whereas 3.3% of the bacteria were killed (testing positive for PI). Column A shows the forward-side scatter (FS-SS) and the applied gating strategy. Column B shows a distinction between viable, Syto9-positive bacteria (lower right panel of each square), killed bacteria testing positive for PI (upper left panel of each square), and bacteria testing positive for both stains (upper right panel of each square). Bacteria located in lower left panel of each square membranous remnants of killed bacteria. In columns C and D, the percentage of bacteria testing positive for Syto-9 and PI, respectively, is observed.

FIG. 3 depicts the obtained flow cytometry results on *S. aureus*. In the untreated sample, 96.5% of the bacteria were viable (testing positive for Syto-9), whereas 3.3% of the bacteria were killed (testing positive for PI). *S. aureus* was highly affected by the treatment with LL-37, in that 31.9% of the bacteria tested positive for PI. Remarkably, LL-37 was even more potent than Vancomycin, and it was almost as effective as when treating bacteria with isopropanol. Unlike LL-37, the treatment with GA was less promising, only returning 12.1% of the bacteria positive for PI staining. Compared to *E. coli*, fewer cells were dimly stained for Syto9, thereby indicating that different killing mechanisms could take place.

Figure 2:
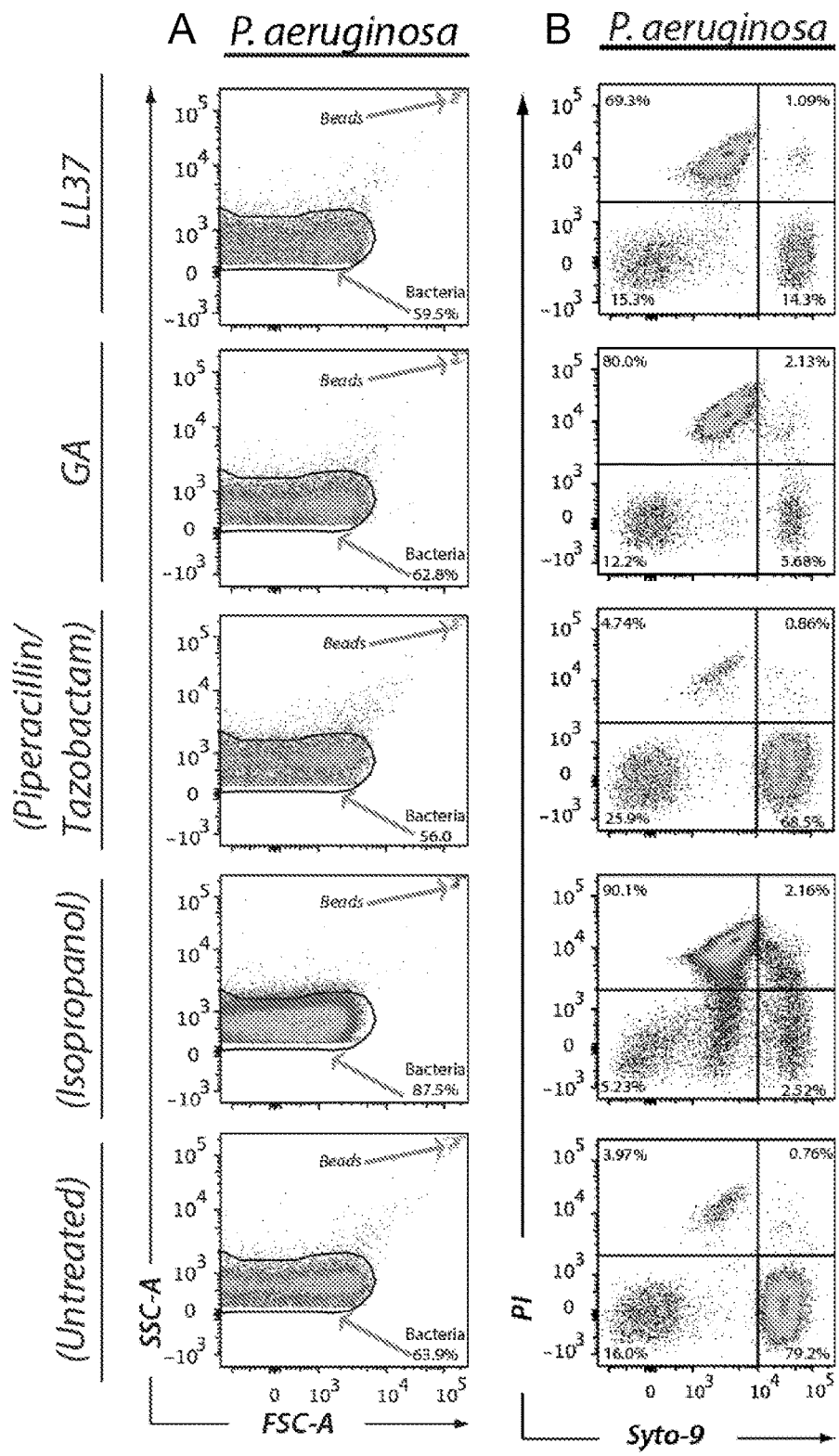
FIG. 2 shows the obtained flow cytometry results on *P. aeruginosa*. Flow cytometry was used to determine the antimicrobial activity of GA and LL-37. The flow cytometry diagrams show the results after treatment with 50 µg/ml LL-37, GA, piperacillin/tazobactam, 7% isopropanol and the untreated control. Column A shows the forward-side scatter (FS-SS) and the applied gating strategy. Column B shows a clear distinction between viable, Syto9-positive bacteria (lower right panel of each square), killed bacteria testing positive for PI (upper left panel of each square), and bacteria testing positive for both stains (upper right panel of each square). Bacteria located in lower left panel of each square are membranous remnants of killed bacteria.
Figure 4:
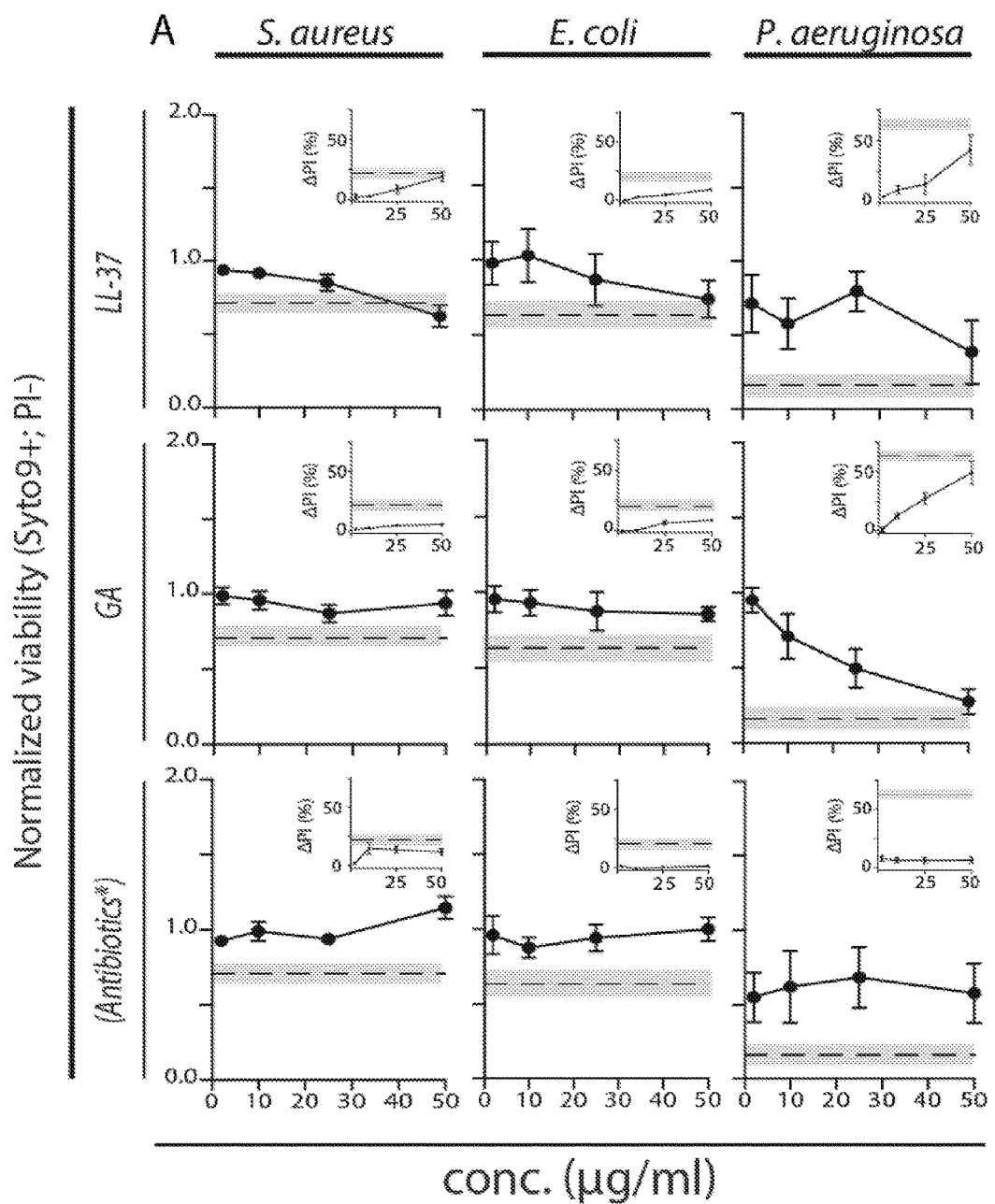
FIG. 4 shows an overview of the results depicted in FIGS. 1, 2 and 3. The x-axis indicates the concentration of antibiotics, GA or LL37, whereas the y-axis indicates viability of the bacteria. The dashed line depicts the average PI positivity after treatment with 10% isopropanol, whereas the grey box depicts the matching standard deviation.

In FIG. 4, all data presented in FIGS. 1 to 3 are gathered, thereby making it clear that GA has an antibacterial effect on *E. coli* and *P. aeruginosa*, and, although to a lower extent, on *S. aureus*. The dashed line depicts the average PI positivity after treatment with 7% isopropanol, whereas the grey box depicts the standard deviation.

GA and LL-37 was equally effective against *E. coli* and *P. aeruginosa*, whereas *S. aureus* was less susceptible to GA as when compared to the antimicrobial activity of LL-37. Intriguingly, LL-37 and GA were found to be highly active against *P. aeruginosa*. The treatment resulted in a markedly increased PI positivity (app. 50%) and a significantly decreased bacterial inoculum within the 30 minutes of treatment (app. 75%). Similarly, we found an increased PI expression on GA-treated *E. coli* and a minor increased PI on GA-treated *S. aureus*. Piperacillin/tazobactam elicited no antimicrobial activity in either *E. coli* or *P. aeruginosa* within the 30 minutes of treatment. Vancomycin attained an activity that was comparable to the one obtained for LL-37, although the latter in comparison also decreased the bacterial load.

Figure 5:
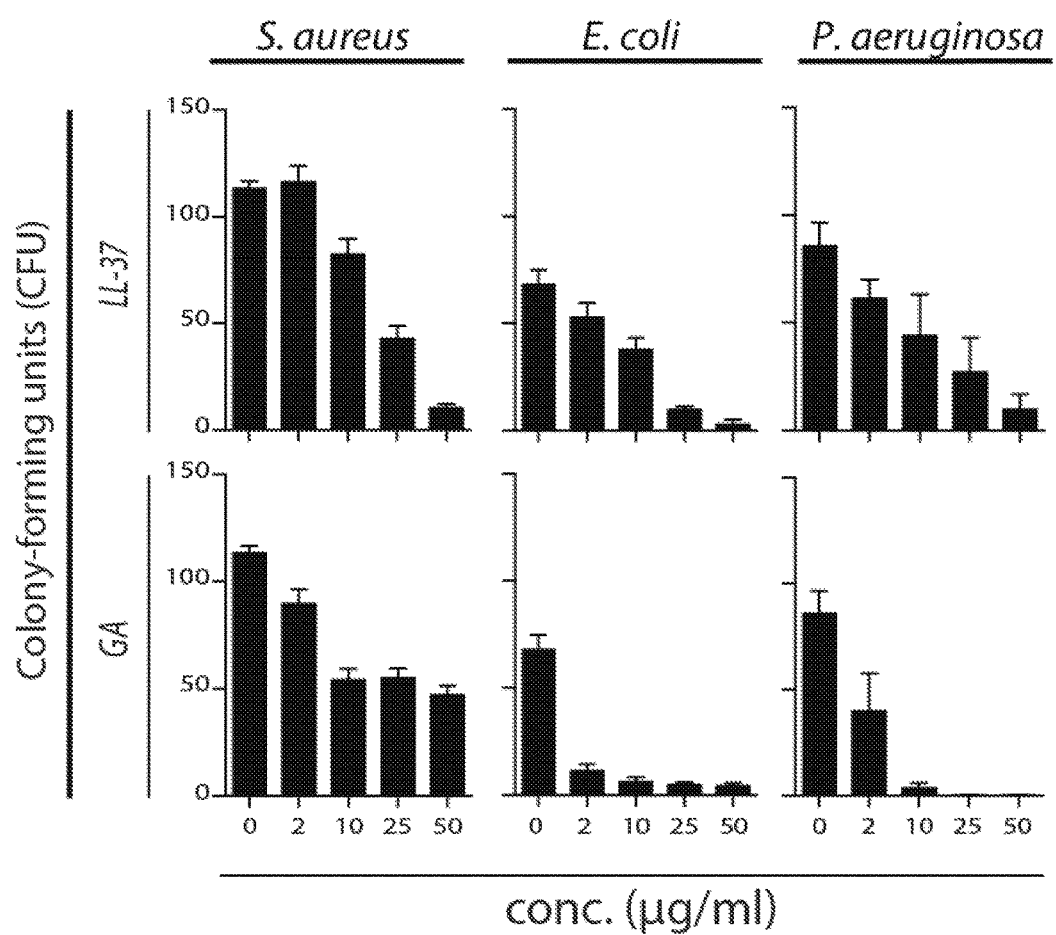
FIG. 5 demonstrates the ability of *S. aureus*, *E. coli* and *P. aeruginosa* to form colony forming units (CFU). The bacteria were treated with LL-37 and GA in the same way as the experiments presented in FIGS. 1 to 5.

FIG. 5 demonstrates the ability of *S. aureus*. *E. coli* and *P. aeruginosa* to form colony forming units. The bacteria were treated with LL-37 and GA in the same way as the experiments presented in FIGS. 1 to 4. The colony forming unit (CFU) counting showed a similar trend as an increasing dose of GA and LL-37 led to a greater antibacterial effect. However, GA had an enhanced ability to kill *E. coli* even at relatively low concentrations, i.e. 2 μg/ml. As observed in the flow cytometry assay, GA seems to preferably kill gram-negative bacteria, i.e. *E. coli* and *P. aeruginosa*, whereas GA has a low antimicrobial impact on *S. aureus*. Interestingly, this scenario was not as notable for LL-37. However, GA seemed to have a higher antimicrobial activity against *E. coli* and *P. aeruginosa* than in comparison with the results obtained for LL-37. All experiments were performed as four replicates.

Example 4

Bacterial Growth

Figure 6:
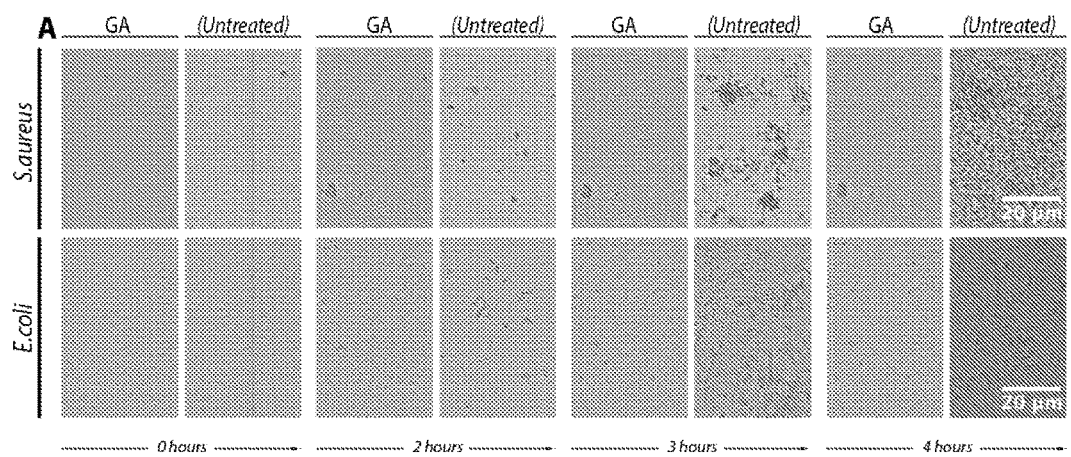
FIG. 6 shows the effect of GA on bacterial growth using an optical screening system (oCelloScope).
Figure 6:
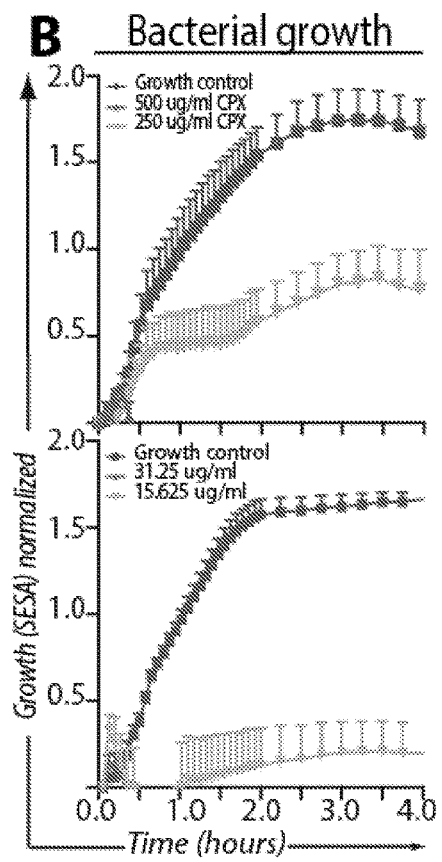

The effect of GA on bacterial growth was further evaluated using, an optical screening system (oCelloScope) (FIG. 6). The oCelloScope system introduces real-time detection of bacterial growth with imaging material to support the automatically generated graphs. The minimal inhibitory concentration is defined as the lowest concentration of which bacterial growth can still be detected. The minimal inhibitory concentration (MIC) of GA was determined for *S. aureus* (Wood 46) and *E. coli* (NCTC 10418). As seen in FIG. 6A, the oCelloScope system enabled time-lapse microscopy pictures showing bacterial growth at different time points. GA attained a high killing efficiency in *E. coli*, whereas *S. aureus* demonstrated a lower susceptibility to GA. Bacterial growth curves were generated by the oCelloScope segmentation and extraction of surface area (SESA) algorithm (FIG. 6B). GA exhibited a high antimicrobial activity against *E. coli*, i.e. MIC=31 μg/ml, as opposed to a lower antimicrobial efficacy in *S. aureus*, i.e. MIC=500 μg/ml. All experiments were performed as three replicates.

Example 5

Antimicrobial Activity in Human Serum and Plasma

Figure 7:
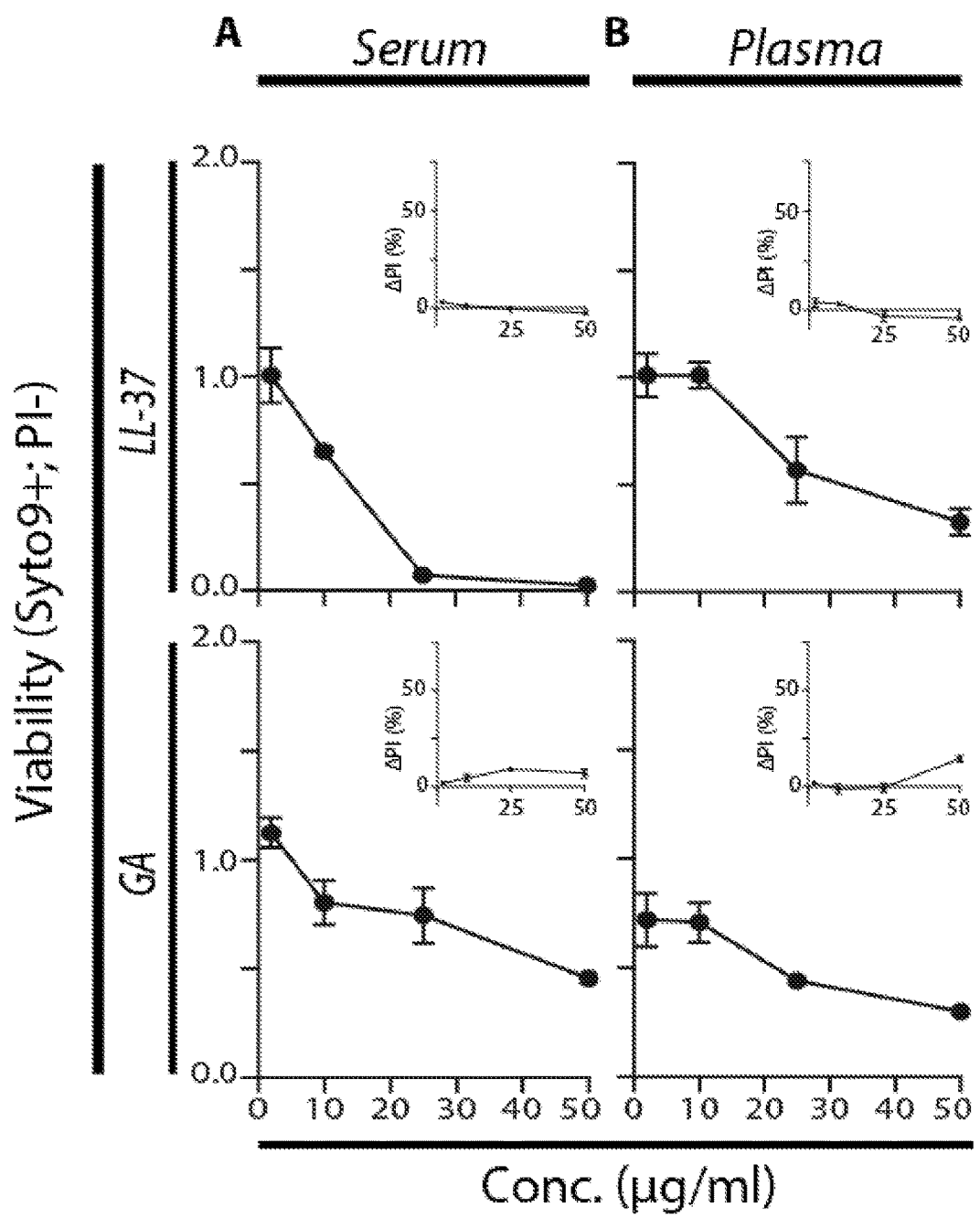
FIG. 7 depicts the viability of bacteria subjected to GA or LL-37 in human serum (column A) or plasma (column B). GA and LL-37 retains antimicrobial activity in both plasma and serum. The results in FIG. 8 demonstrate that bacterial viability decreased concurrently with an increased concentration of GA and LL-37. All experiments were performed as four replicates.

It has been reported that the antimicrobial activity of antimicrobial peptides are inhibited by their binding to different factors in human plasma (Wang, Y., et al., *Apolipoprotein A-I binds and inhibits the human antibacterial/cytotoxic peptide LL-37*. J Biol Chem, 1998. 273(50): p. 33115-8), serum and is influenced by pH and ion composition (Johansson, J., et al., *Conformation-dependent antibacterial activity of the naturally occurring human peptide LL-37*. J Biol Chem, 1998. 273(6): p. 3718-24). To investigate the potential of GA for systemic application, bacterial isolates of *P. aeruginosa* (PAO1, ~$10^8$ cells/ml) were incubated with increasing concentrations of GA and compared to LL-37. Bacterial survival and enumeration was evaluated by a flow cytometry bead standard and stained with propidium iodide and Syto9 following procedures as previously described above in the antimicrobial susceptibility testing by flow cytometry-based assay. As indicated in FIG. 7, GA and LL-37 retains antimicrobial activity in both plasma and serum. The results in FIG. 7 demonstrate that bacterial viability decreased concurrently with an increased concentration of GA and LL-37. All experiments were performed as four replicates.

Example 6

Antimicrobial Activity in Salt Solutions

Figure 8:
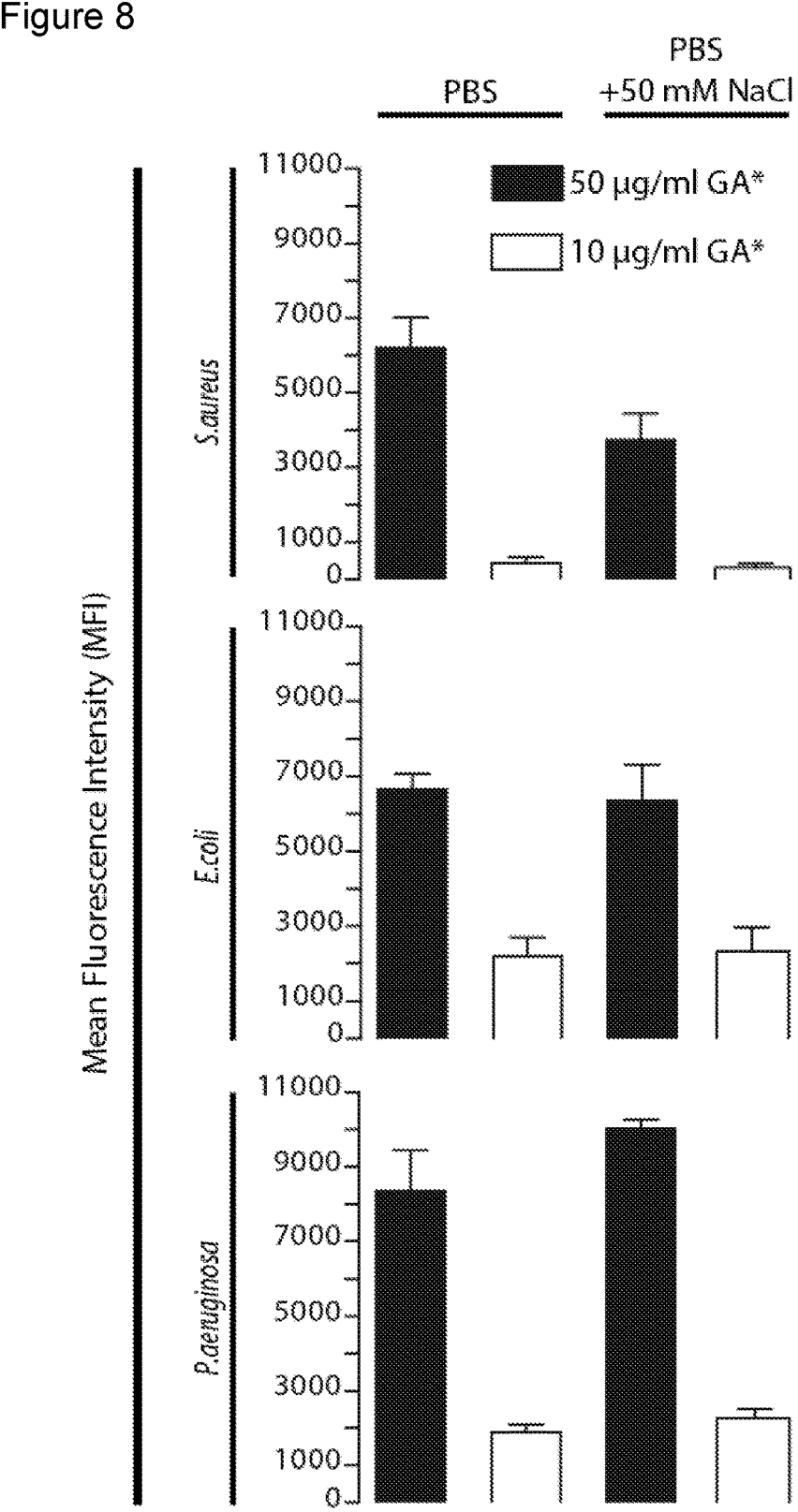
FIG. 8 display binding capacity of GA to bacteria resuspended in PBS or in PBS supplemented with 50 mM NaCl. To determine the binding capacity of GA to bacteria, GA was labeled with Alexa Fluor 488 and subsequently incubated with *P. aeruginosa* (PAO1), *S. aureus* (Wood 46) and *E. coli* (NCTC 10418) at GA concentrations of 50 µg/ml and 10 µg/ml. Mean Fluorescence intensities (MFI, Y-axis) were assessed by flow cytometry to quantify the binding capacity of GA to the bacterial membrane. All experiments were performed as four replicates.

The antimicrobial activity of AMPs is typically reduced at higher concentrations of salt. This constitutes a problem when for example treating patients with cystic fibrosis. These patients have a high salt concentration in their lungs of about 150-200 mM, and it is therefore critical that drugs used for treating these patients are active at such high salt concentrations (Gilljam H et al., Scand J Clin Lab Invest. 1989 April; 49(2):121-4). Therefore, the binding capacity of GA to bacteria resuspended in PBS or in PBS supplemented with 50 mM NaCl. PBS+50 mM NaCl results in a total salt concentration of 200 mM. To determine the binding capacity of GA to bacteria, GA was labeled with Alexa Fluor 488 and subsequently incubated with *P. aeruginosa* (PAO1), *S. aureus* (Wood 46) and *E. coli* (NCTC 10418) at GA concentrations of 50 μg/ml and 10 μg/ml (FIG. 8).

Mean Fluorescence intensities (MFI) were assessed by flow cytometry to quantify the binding capacity of GA to the bacterial membrane. As seen in FIG. 8, GA retained its binding capacity to *E. coli* and *P. aeruginosa* even at salt concentrations of 200 mM. All experiments were performed as four replicates.

Example 7

Transmission Electron Microscopy

Figure 9:
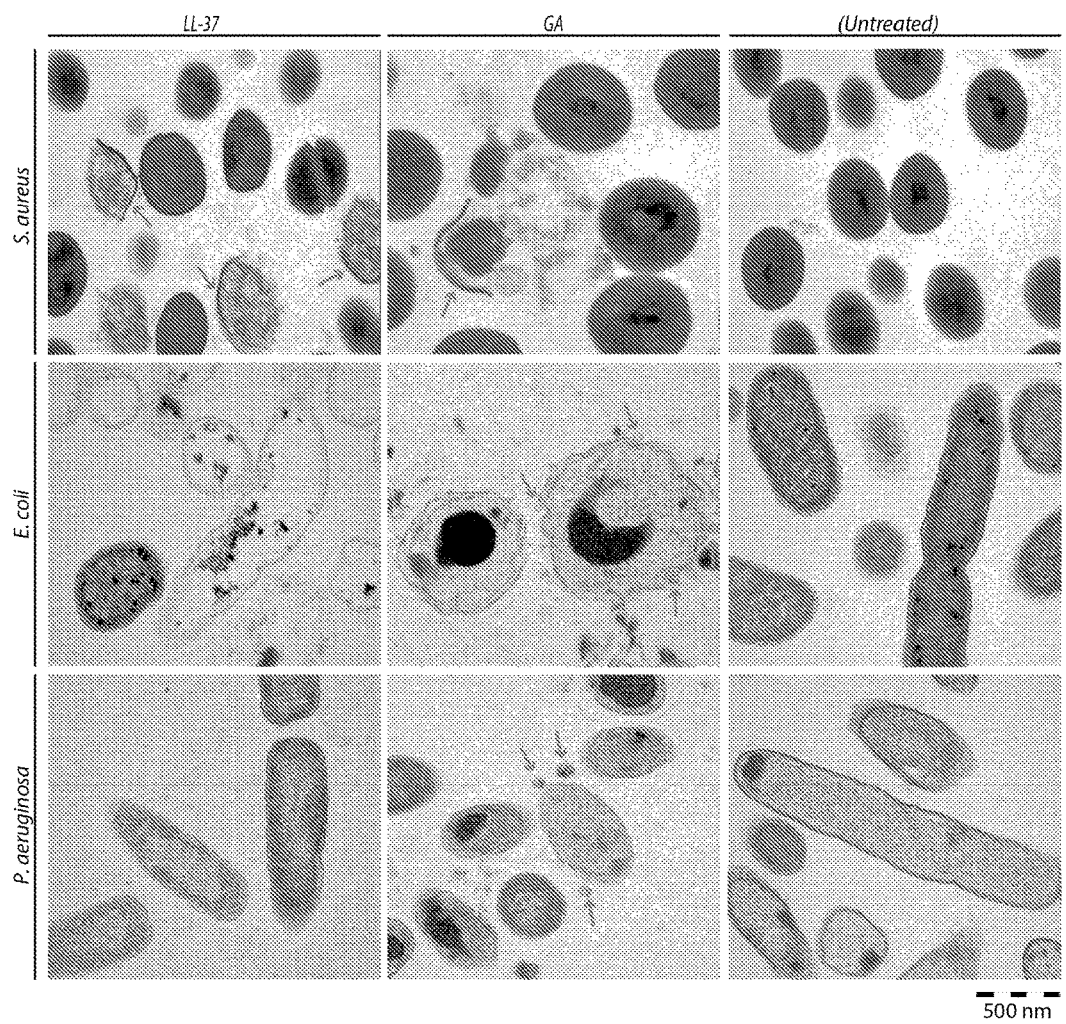
FIG. 9 displays Transmission Electron Microscopy (TEM) pictures of *P. aeruginosa* (PAO1), *S. aureus* (Wood 46) and *E. coli* (NCTC 10418) cells after treatment with GA and LL-37. Untreated *E. coli* and *P. aeruginosa* exhibited a normally shaped, well-defined and undamaged outer bacterial membrane. Signs of damage to the bacterial membrane were clearly observed on *E. coli* cells after treatment with LL-37 and GA, but the most distinctive observations was the generation of *E. coli* bacteria devoid of cytoplasmic content (FIG. 10). After treatment with GA, numerous nanovesicles with a diameter of 50-100 nm were found to protrude or to be released from the outer membrane of *P. aeruginosa* and *E. coli* (indicated by arrows). Scale bar, 0.5 µm. Experiments were performed as 2 replicates.

Transmission electron microscopy (TEM) was applied to examine the ultrastructural changes in *P. aeruginosa* (PAO1), *S. aureus* (Wood 46) and *E. coli* (NCTC 10418) induced after treatment with GA and LL-37. Untreated *E. coli* and *P. aeruginosa* exhibited a normally shaped, well-defined and undamaged outer bacterial membrane (FIG. 9). Signs of damage to the bacterial membrane were clearly observed on *E. coli* cells after treatment with LL-37 and GA, but the most distinctive observations was the generation of *E. coli* bacteria devoid of cytoplasmic content (FIG. 9). After treatment with GA, numerous nanovesicles with a diameter of 50-100 nm were found to protrude or to be released from the outer membrane of *P. aeruginosa* and *E. coli*, but this observation was not supported for LL-37. This critical alteration in the outer membrane of *E. coli* has previously been described as a disintegration of the outer membrane into micelles and vesicle-like structures (Meincken, M., D. L. Holroyd, and M. Rautenbach, *Atomic force microscopy study of the effect of antimicrobial peptides on the cell envelope of Escherichia coli*. Antimicrob Agents Chemother, 2005. 49(10): p. 4085-92). It has been interpreted as a difference in strain susceptibilities to various antimicrobial peptides (Hartmann, M., et al., Damage of the bacterial cell envelope by antimicrobial peptides gramicidin S and PGLa as revealed by transmission and scanning electron microscopy. Antimicrob Agents Chemother, 2010. 54(8): p. 3132-42). After incubation with LL-37 and GA we saw a dramatically reduced number of *P. aeruginosa* and remnants of intracellular content in the surrounding extracellular matrix. Untreated *S. aureus* showed round, proliferating cells with undamaged and well-defined membranes. After incubation with LL-37 and GA, we found burst cells, but this observation was most significant after treatment with LL-37 (FIG. 9). Scale bar, 0.5 μm. Experiments were performed as 2 replicates.

Example 8

Antibacterial Effect on Multiresistant *Pseudomonas aeruginosa*

Figure 10:
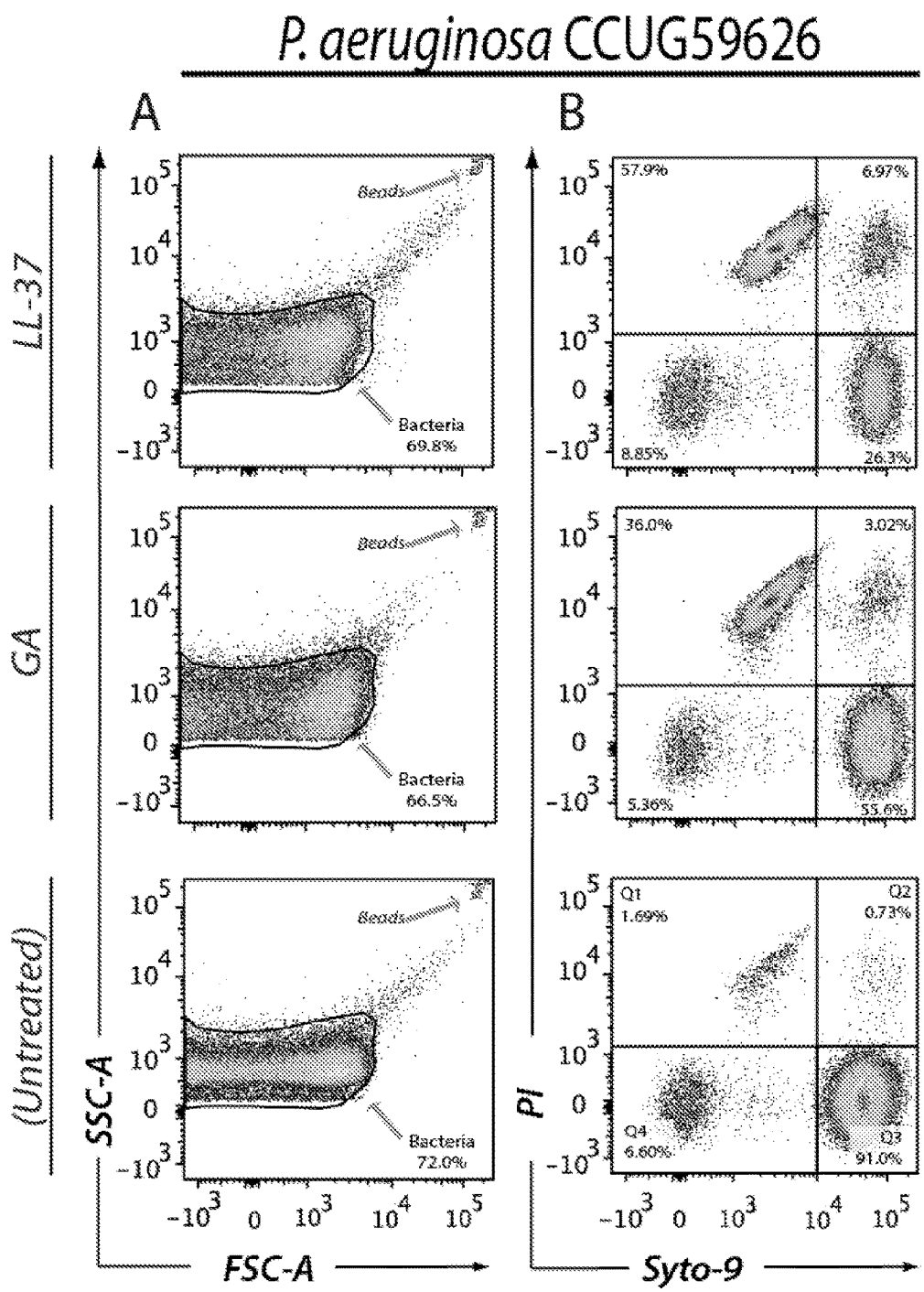
FIG. 10 shows flow cytometry results on a multiresistant *P. aeruginosa* strain (CCUG59626). Flow cytometry was used to determine the antimicrobial activity of GA and LL-37. The flow cytometry diagrams show the results after treatment with 50 µg/ml LL-37 or GA and the untreated control. Column A shows the forward-side scatter (FS-SS) and the applied gating strategy. Column B shows a clear distinction between viable, Syto9-positive bacteria (lower right panel of each square), killed bacteria testing positive for PI (upper left panel of each square), and bacteria testing positive for both stains (upper right panel of each square).
Figure 11:
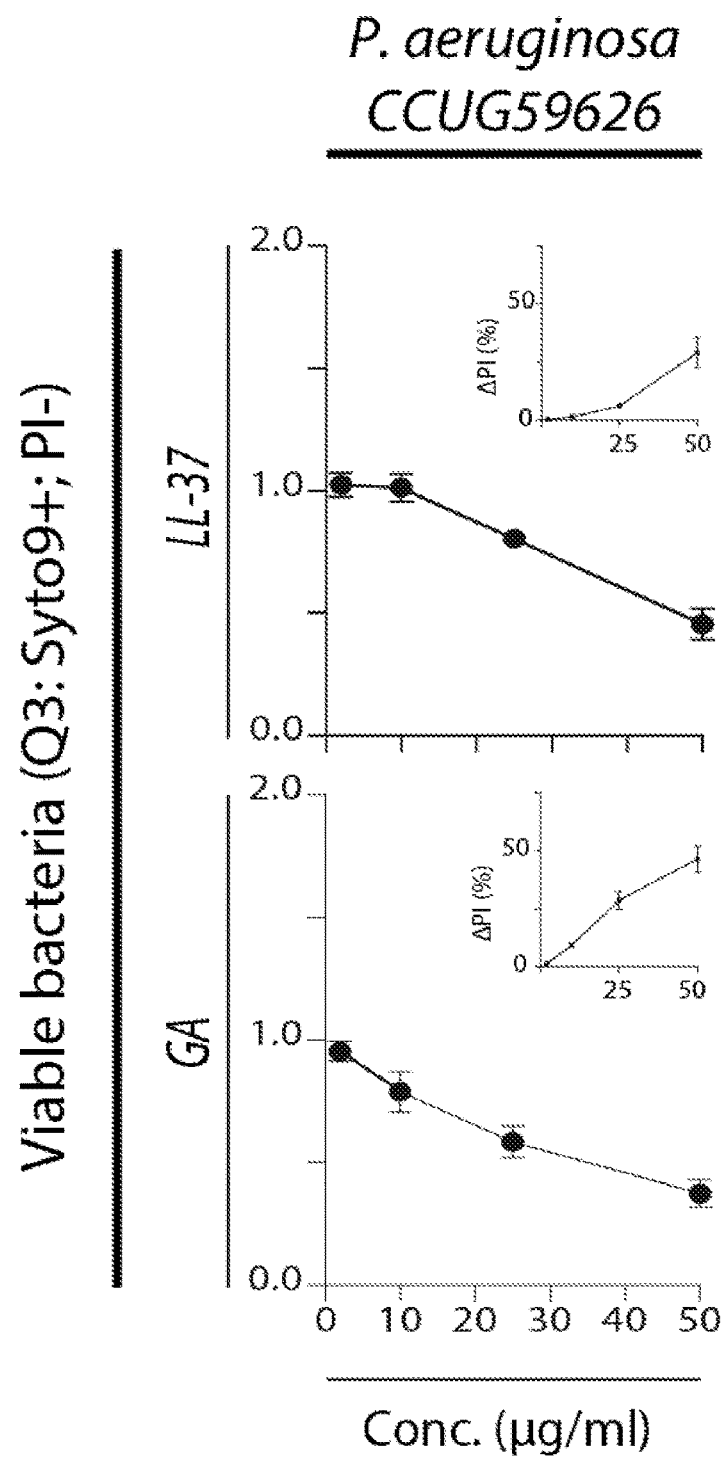
FIG. 11 is a diagram of results presented in FIG. 10 showing the viability (y-axis) of multiresistant *P. aeruginosa* strain (CCUG59626) at increasing concentrations of GA or LL-37 (x-axis).

A multi-resistant *P. aeruginosa* strain (CCUG59626) (~$10^8$ cells/ml) was incubated with varying concentrations of GA and LL-37. The same protocol as used for experiments presented in FIG. 2 was applied. The obtained results are shown in FIGS. 10 and 11. The results are similar to those obtained for *P. aeruginosa* (strain PAO1) thereby demonstrating that the multiresistant strain is highly susceptible to GA. All experiments were performed as four replicates.

Concluding Remarks

It is demonstrated that GA is a powerful anti-microbial agent towards gram-negative organisms, such as *Escherichia coli* and *Pseudomonas aeruginosa*. GA exhibits activity against gram-positive bacteria, such as *Staphylococcus aureus*, however to a lower extent. Obviously, this could be due to structural differences between the membranes of, respectively, Gram-negative and Gram-positive bacteria, thus making Gram-positive bacteria less susceptible to the membranolytic activities of GA.

With the reduced ability of GA to interfere with human cells compared to LL-37 and the generally well-tolerated treatment of RR-MS patients, GA or GA-like random co-polymers may act as novel and safe antimicrobial agents towards gram-negative organisms resistant to known antibiotics. Moreover, the randomness of the copolymers in the GA formulation may, provide GA with a previously unappreciated potential of killing drug-resistant organisms, which may have acquired resistance to first-line antibiotics, without losing its long-lasting efficacy on other multi-resistant microbial organisms.

The invention claimed is:

1. A method for treating, ameliorating, or preventing bacterial infections with *Escherichia coli, Pseudomonas aeruginosa*, or *Staphylococcus aureus*, said method comprising administration of an effective amount of a composition comprising a glatiramer acetate copolymer to an individual in need thereof.

2. The method according to claim 1, wherein said individual has cystic fibrosis.

3. The method according to claim 1, wherein said composition further comprises a pharmaceutically acceptable carrier.

4. The method according to claim 1, wherein said composition further comprises at least one further active agent.

5. The method according to claim 4, wherein said further active agent is an antibiotic.

6. The method according to claim 5, wherein said antibiotic is selected from the group consisting of betalactams, carbepenems, kinolones, macrolides, Vancomycin, Linezolide, daptomycin, aztronam and sulfur compounds.

7. The method according to claim 5, wherein said antibiotic is an aminoglycoside.

8. The method according to claim 7, wherein said aminoglycoside is tobramycin.

9. The method according to claim 1, wherein said composition is formulated for administration using a nebulizer.

10. The method according to claim 1, wherein said composition is formulated for topical administration as a lotion, cream, or ointment.

11. The method according to claim 10, wherein said composition is formulated for administration to the eye as an eye lotion.

12. The method of claim 1, wherein said administration kills or inhibits the growth of *Escherichia coli, Pseudomonas aeruginosa*, or *Staphylococcus aureus*.

* * * * *